(12) United States Patent
Gjerstad et al.

(10) Patent No.: US 10,465,237 B2
(45) Date of Patent: Nov. 5, 2019

(54) METHODS AND SYSTEMS FOR QUANTIFICATION WITHOUT STANDARD CURVES

(71) Applicant: LIFE TECHNOLOGIES CORPORATION, Carlsbad, CA (US)

(72) Inventors: Carmen Gjerstad, Millbrae, CA (US); Shoulian Dong, Mountain View, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 442 days.

(21) Appl. No.: 15/113,030

(22) PCT Filed: Jan. 20, 2015

(86) PCT No.: PCT/US2015/012088
§ 371 (c)(1),
(2) Date: Jul. 20, 2016

(87) PCT Pub. No.: WO2015/109330
PCT Pub. Date: Jul. 23, 2015

(65) Prior Publication Data
US 2017/0022552 A1 Jan. 26, 2017

Related U.S. Application Data

(60) Provisional application No. 61/936,778, filed on Feb. 6, 2014, provisional application No. 61/929,439, filed on Jan. 20, 2014.

(51) Int. Cl.
*C12Q 1/68* (2018.01)
*C12Q 1/6851* (2018.01)
(Continued)

(52) U.S. Cl.
CPC ........... *C12Q 1/6851* (2013.01); *G16B 20/00* (2019.02); *G16B 25/20* (2019.02)

(58) Field of Classification Search
CPC ...................................................... C12Q 1/68
See application file for complete search history.

(56) References Cited

U.S. PATENT DOCUMENTS

| 2007/0134658 | A1 | 6/2007 | Bohmer |
| 2009/0130659 | A1 | 5/2009 | Rehli |
| 2012/0070840 | A1 | 3/2012 | Bechler et al. |

FOREIGN PATENT DOCUMENTS

| CN | 103451303 | 12/2013 |
| EP | 0959140 | 11/1999 |

(Continued)

OTHER PUBLICATIONS

Ferreira et al., Real-time quantitative PCR with SYBR Green I detection for estimating copy numbers of nine drug resistance candidate genes in Plasmodium, Malar J. 2006; 5: 1. Published online Jan. 18, 2006.*

Liu et al., A new quantitative method of real time reverse transcription polymerase chain reaction assay based on simulation of polymerase chain reaction kinetics, Anal Biochem. Mar. 1, 2002;302(1):52-9.*

(Continued)

*Primary Examiner* — Aaron A Priest

(57) ABSTRACT

A method for quantitation of biological material in a biological sample is provided. The method includes receiving amplification data from amplification of a first and a second reference sample and receiving amplification data from amplification of a biological sample. The method further includes determining an efficiency from the received amplification data from amplification of the first and second reference sample. The method includes determining a relative PCR efficiency for the biological sample. Next, the method includes determining a quantity of biological mate- (Continued)

rial in the biological sample using the relative PCR efficiency.

24 Claims, 20 Drawing Sheets

Specification includes a Sequence Listing.

(51) Int. Cl.
    *G16B 20/00*      (2019.01)
    *G16B 25/20*      (2019.01)

(56) References Cited

FOREIGN PATENT DOCUMENTS

| | | | |
|---|---|---|---|
| EP | 1138783 | 10/2001 | |
| EP | 1138783 B1 * | 8/2007 | ........... C12Q 1/6851 |

OTHER PUBLICATIONS

Liu, W. et al., "A New Quantitative Method of Real Time Reverse Transcription Polymerase Chain Reaction Assay Based on Simulation of Polymerase Chain Reaction Kinetics", *Analytical Biochemistry*, vol. 302, Jan. 30, 2002, 52-59.

PCT/US2015/012088 "International Search Report and Written Opinion dated Mar. 31, 2015", dated Mar. 31, 2015, 13 Pages.

Pfaffl, Michael W. , "Quantification Strategies in Real-Time PCR" *A-Z of Quantitative PCR*, Chapter 3, 2004, 87-112.

Sekhavati, M. et al., "Development and use of quantitative competitive PCR assays for relative quantifying rumen anaerobic fungal populations in both in vitro and in vivo systems", *Mycological Research*, vol. 113, Jul. 30, 2009, 1146-1153.

Skulj, M. et al., "Improved determination of plasmid copy number using quantitative real-time PCR for monitoring fermentation processes", *Microbial Cell Factories*, vol. 7 (6), Mar. 7, 2008, 1-12.

* cited by examiner

| %C<br>%U | 1<br>100%<br>0% | 2<br>199%<br>1% | 3<br>90%<br>10% | 4<br>75%<br>25% | 5<br>60%<br>40% | 6<br>50%<br>50% | 7<br>35%<br>65% | 8<br>20%<br>80% | 9<br>10%<br>90% | 10<br>5%<br>95% | 11<br>1%<br>99% | 12<br>0%<br>100% |
|---|---|---|---|---|---|---|---|---|---|---|---|---|
| A | A02_F0_R0 | | | | | | | | | | | |
| B | A02_F0_R2 | | | | | | | | | | | |
| C | A44_F3_R0 | | | | C Primer | | | | | | | |
| D | A44_F3_R2 | | | | | | | | | | | |
| E | A51_F1_R1 | | | | | | | | | | | |
| F | A51_F1_R4 | | | | | | | | | | | |
| G | A54_F0_R2 | | | | | | | | | | | |
| H | A54_F2_R5 | | | | | | | | | | | |
| I | A02_F0_R0 | | | | | | | | | | | |
| J | A02_F0_R2 | | | | | | | | | | | |
| K | A44_F3_R0 | | | | T Primer | | | | | | | |
| L | A44_F3_R2 | | | | | | | | | | | |
| M | A51_F1_R1 | | | | | | | | | | | |
| N | A51_F1_R4 | | | | | | | | | | | |
| O | A54_F0_R2 | | | | | | | | | | | |
| P | A54_F2_R5 | Forgot to add primer, Use as NTC | | | | | | | | | | |

FIG. 4

Table 1. Targets, Assay design, Sample Type and Experiments

| Assay ID | Gene Symbol | Refseq | Chr | Strand | SYBR® Select Evaluation | Quantification Method | No. of assays | GC content range | Tm range (°C) | Primer Length range | Sample Type gDNA | Sample Type Synthetic |
|---|---|---|---|---|---|---|---|---|---|---|---|---|
| A02 | APC | NM_001127511 | 5 | + | x | x | 12 | 43-65% | 56.2-60.8 | 16-23 | | x |
| A29 | ICAM1 | NM_000201 | 19 | + | x | x | 16 | 26-100% | 58.6-62.3 | 10-31 | x | |
| A44 | RPRM | NM_019845 | 2 | | | x | 15 | 31-61% | 57.9-60.9 | 18-26 | x | x |
| A51 | SORBS3 | NM_005775 | 8 | + | x | x | 15 | 38-61% | 53.5-61.8 | 16-23 | x | x |
| A54 | SUB1 | NM_006713 | 5 | + | x | x | 16 | 56-75% | 58-60.7 | 13-18 | | x |
| A16 | DPH1 | NM_001383 | 17 | + | x | | 6 | 43-63% | 57.9-60.1 | 16-21 | x | |
| A37 | PTEN | NM_000314 | 10 | + | x | | 11 | 32-67% | 59.5-61.7 | 15-25 | x | |
| A42 | RPP14 | NM_001098783 | 3 | + | x | | 16 | 50-79% | 57.9-62.1 | 13-22 | x | |
| A45 | SCGB3A1 | NM_052863 | 5 | | x | | 15 | 41-85% | 54.2-61.5 | 13-23 | x | |
| A49 | SYK | NM_003177 | 9 | + | x | | 16 | 16-92% | 57.8-60.9 | 12-32 | x | |
| A47 | SCGB3A1 | NM_052863 | 5 | | | x | 1 | | | | x | |

FIG. 11

| Application | Assay 1 | Assay 2 | | Ref1 | Ref2 | Ref3 | Ref4 | Ref5 |
|---|---|---|---|---|---|---|---|---|
| Methylation Level | "C" assay | "U" assay | Sample | 100% MeC | 10% MeC + 90% UnM | 100% UnM | 100% MeC (optional) | 100% UnM (optional) |
| | | | Assay | "C" assay | "C" assay | "U" assay | "U" assay | "U" assay |
| CNV | Reference assay | Target assay | Sample | Known X and Y | Not required | Known X and Y | Not required | Not required |
| | | | Assay | Reference assay | | Target assay | | |
| Genotyping | SNP1 assay | SNP2 assay | Sample | 100% SNP1 | 50% SNP1 + 50% SNP2 | 100% SNP2 | 100% SNP1 | 100% SNP2 |
| | | | Assay | SNP1 assay | SNP1 assay | SNP2 assay | SNP2 assay | SNP1 assay |

FIG. 17

SEQUENCE LISTING

```
<160> NUMBER OF SEQ ID NOS: 8

<210> SEQ ID NO 1
<211> LENGTH: 89
<212> TYPE: DNA
<213> ORGANISM: Artificial Sequence
<220> FEATURE:
<223> OTHER INFORMATION: Synthetic Template

<400> SEQUENCE: 1
agaattgagg gtggtataga agcgggtaaa ggggcgatcg gattcgagtt tagggaggcg      60
tatatagggg gcgtcgaggt tcgagaagg                                        89

<210> SEQ ID NO 2
<211> LENGTH: 98
<212> TYPE: DNA
<213> ORGANISM: Artificial Sequence
<220> FEATURE:
<223> OTHER INFORMATION: Synthetic Template

<400> SEQUENCE: 2
gcgagggaga aatcggtcgt tttttttcga aaggtcgaag tcgagagaaa taattgattt      60
cgataggttt gtttcgttta gttttgata gtgagggg                               98

<210> SEQ ID NO 3
<211> LENGTH: 71
<212> TYPE: DNA
<213> ORGANISM: Artificial Sequence
<220> FEATURE:
<223> OTHER INFORMATION: Synthetic Template

<400> SEQUENCE: 3
cgggtaggga tgtttttgcg ttttcgggcg gtttcgggtt tagttatttg ttcgtcgggg      60
```

```
aaggtaggtt c                                                          71

<210> SEQ ID NO 4
<211> LENGTH: 106
<212> TYPE: DNA
<213> ORGANISM: Artificial Sequence
<220> FEATURE:
<223> OTHER INFORMATION: Synthetic Template

<400> SEQUENCE: 4
ggtagattga gggcggtcgg ggagtgagga gtcgcgggga gagagtcgcg gcgttttcgg      60
gataatgcgg cggcggtttg tttaggtggg gcgcgtgcgg ttatttt                   106

<210> SEQ ID NO 5
<211> LENGTH: 71
<212> TYPE: DNA
<213> ORGANISM: Artificial Sequence
<220> FEATURE:
<223> OTHER INFORMATION: Synthetic Template

<400> SEQUENCE: 5
ugggtaggga tgttttttgug ttttugggug gtttugggtt tagttatttg ttugtugggg    60
aaggtaggtt c                                                          71

<210> SEQ ID NO 6
<211> LENGTH: 106
<212> TYPE: DNA
<213> ORGANISM: Artificial Sequence
<220> FEATURE:
<223> OTHER INFORMATION: Synthetic Template

<400> SEQUENCE: 6
ggtagattga gggtggtugg ggagtgagga gtuguggga gagagtugug gugttttugg      60
gataatgugg ugguggtttg tttaggtggg gugugtgugg ttattt                   106

<210> SEQ ID NO 7
<211> LENGTH: 89
<212> TYPE: DNA
<213> ORGANISM: Artificial Sequence
<220> FEATURE:
<223> OTHER INFORMATION: Synthetic Template

<400> SEQUENCE: 7
agaattgagg gtggtataga aguggtaaa ggggugatug gattugagtt tagggaggug       60
tatatagggg gugtugaggt tugagaagg                                        89

<210> SEQ ID NO 8
<211> LENGTH: 98
<212> TYPE: DNA
<213> ORGANISM: Artificial Sequence
<220> FEATURE:
<223> OTHER INFORMATION: Synthetic Template

<400> SEQUENCE: 8
gugagggaga aatuggtugt ttttttuga aaggtugaag tugagagaaa taattgattt       60
ugataggttt gtttugttta gttttttgata gtgagggg                             98
```

METHODS AND SYSTEMS FOR QUANTIFICATION WITHOUT STANDARD CURVES

CROSS-REFERENCE TO RELATED APPLICATIONS

This application is a 371 of International Application No. PCT/US2015/012088 filed Jan. 20, 2015, and claims the benefit of priority to U.S. Provisional Application No. 61/936,778, filed Feb. 6, 2014 and to U.S. Provisional Application No. 61/929,439 filed Jan. 20, 2014, which disclosures are herein incorporated by reference in their entirety.

REFERENCE TO A SEQUENCE LISTING

This application contains a Sequence Listing which has been submitted electronically in ASCII format and is hereby incorporated by reference in its entirety. Said ASCII copy, created on Sep. 16, 2019, is named LT00880US_ST25.txt and is 2,589 bytes in size.

BACKGROUND

Quantitative nucleic acid analysis is extensively used in biological research and clinical analysis. Some of the applications which make use of this technology include: measurement of gene expression, monitoring of biological responses to stimuli, genomic-level gene quantitation, and pathogen detection. Typically, these methodologies utilize Polymerase Chain Reaction (PCR) as a means for selectively amplifying nucleic acid sequences in a manner that allows for their detection.

While it is generally desirable to automate the quantitation process, conventional methodologies often require a degree of user input in the form of subjective interpretation and/or approximation. For example, many reference samples may need to be run to determine a standard curve. The standard curve is then used to determine quantities of unknown samples. In some other applications, reference assays and reference samples are used to provide a reference point or as training sets for relative quantitation, such as in CNV and genotyping. As a result, these techniques may suffer from reduced accuracy and significant user-induced variability. As most optimized assays are specific with high PCR efficiencies, some assays are limited by the template sequence or the primer design. The difference in PCR efficiencies and Ct0 (Ct value at one unit of template concentration) between reference and test assays reduces quantitation accuracy with conventional methods. Furthermore, in high-throughput applications where many samples are to be processed simultaneously, it is desirable to provide increased automation capabilities to improve the speed with which the analysis may be conducted.

The aforementioned limitations of conventional techniques illustrate the need for an improved method for analyzing data generated by PCR-based quantitation techniques that may increase the potential for automation while improving the quantitative accuracy, simplicity, and reproducibility of the analysis.

SUMMARY

In one exemplary embodiment, a method for quantitation of biological material in a biological sample is provided. The method includes receiving amplification data from amplification of a first and a second reference sample and receiving amplification data from amplification of a biological sample. The method further includes determining an efficiency from the received amplification data from amplification of the first and second reference sample. The method includes determining a relative PCR efficiency for the biological sample. Next, the method includes determining a quantity of biological material in the biological sample using the relative PCR efficiency.

In some embodiments, the relative PCR efficiency is determined with the following equation:

$$\varepsilon_{S2A2} = \varepsilon_{S1A1}^{\frac{CT_{100\%S1A1}}{CT_{100\%S2A2}}}.$$

BRIEF DESCRIPTION OF THE DRAWINGS

FIG. 4 illustrates an exemplary plate layout method of quantitation according to various embodiments described herein;

FIG. 11 illustrates a table of a plurality of experiments used with the quantitation method according to various embodiments described herein;

FIG. 17 illustrates a table of various assay types and reference samples for different application that may use the quantitation method according to various embodiments described herein;

DETAILED DESCRIPTION

To provide a more thorough understanding of the present invention, the following description sets forth numerous specific details, such as specific configurations, parameters, examples, and the like. It should be recognized, however, that such description is not intended as a limitation on the scope of the present invention, but is intended to provide a better description of the exemplary embodiments.

As mentioned above, traditionally, standard curves are established for a sample type so that quantities of unknown samples may be determined. By determining an assay specific relative efficiency and a cycle threshold (Ct) for a sample, quantities of samples may be determined without generating a standard curve. The use of relative PCR efficiency improves the accuracy of relative quantitation and allows the use of assays with different efficiencies in relative quantitation. Using the relative PCR efficiency, according to various embodiments described herein, eliminates the need of using assays of matching performances (similar efficiencies and Ct). Thus, virtually any assay may be used using the quantitation method according to various embodiments of the present teachings.

Figure 16:
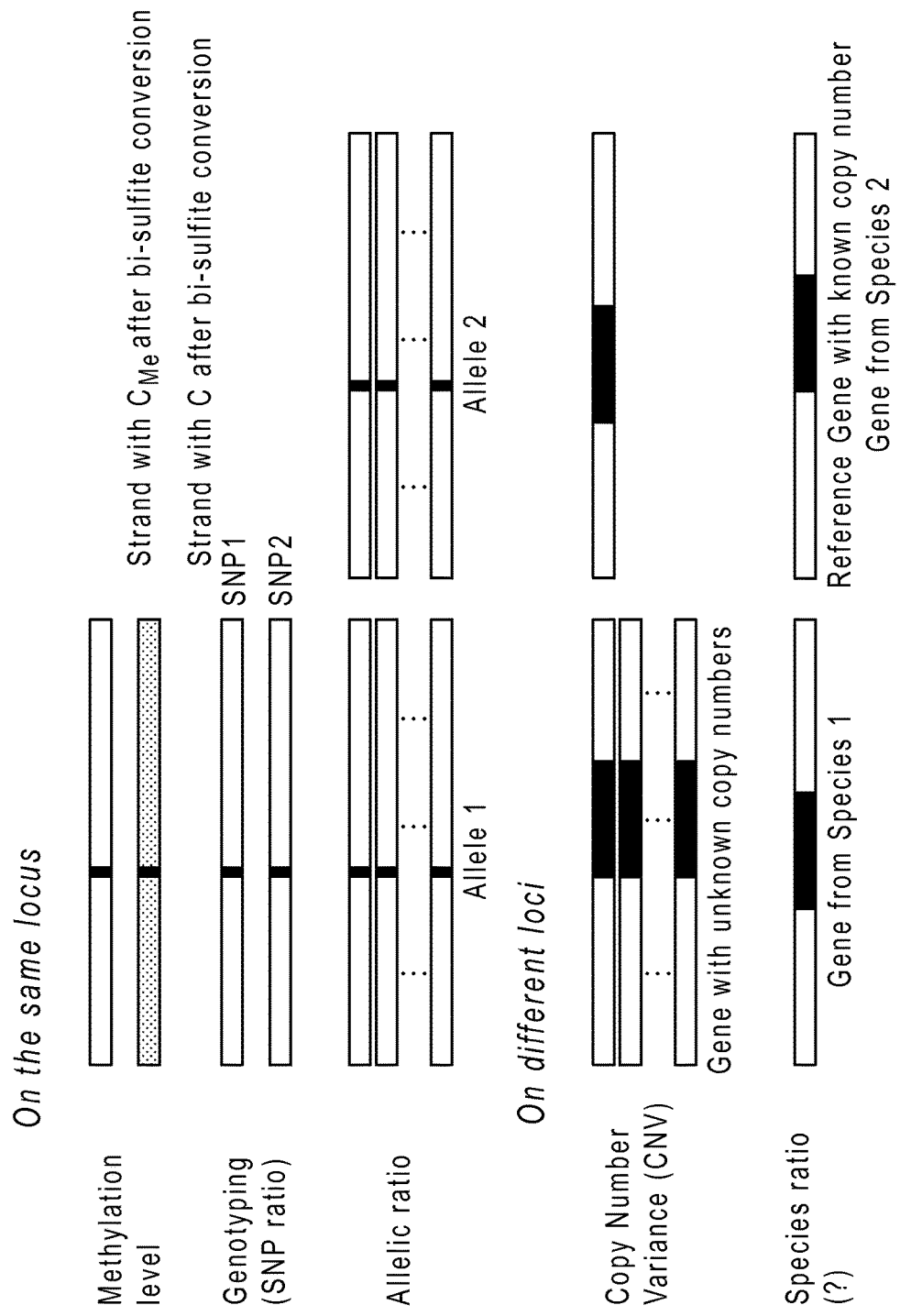
FIG. 16 illustrates various applications that may use the quantitation method according to various embodiments described herein.

According to various embodiments, the quantitation method may be used in a plurality of applications such as, but not limited to, determining methylation levels, genotyping (SNP ratios), determining allelic ratios, determining copy number variance (CNV), and determining species ratios. Various applications that may use the quantitation according to various embodiments described herein are illustrated in FIG. 16.

Methylation Level Determination Example

For example, DNA methylation has strong association with regulation of gene expressions, chromosomal stability and cell development. The change in DNA methylation level of specific loci can be used a biomarkers for early diagnosis, progression and prognosis of cancer and aging. However, measuring the 10-20% change in methylation level with conventional qPCR methods cannot be achieved without generating one or two sets of standard curves.

According to various embodiments, a more simple method is provided to detect the small change in DNA methylation level with SYBR without the complications of generating a standard curve. The quantitation method can provide a simple and accurate method to determine the relative abundance of two states with two assays of equal or different PCR efficiencies with either SYBR or Taqman assays, for example.

Instead of running a standard curve, the actual reaction efficiency is calculated from two reference points according to various embodiments. For example, for a DNA Methylation assay, 10% and 100% methylated control samples may be used as reference points. The percentage of methylation of any sample can be calculated from the equation $\varepsilon^{(Ct_c - Ct_s)}$ where c=reference with 100% methylation and s=sample with n % methylation. This quantitation method has been tested with 12 assays with both synthetic templates and bisulfite converted gDNA of various level of methylation. In the exemplary results, the level of methylation can be accurately measured at all levels tested with a standard error of prediction <4%.

General Overview

As mentioned above, according to various embodiments, the quantitation method can also be applied to calculate the relative ratio of two components in other applications, such as genotyping (SNP ratios), determining allelic ratios, determining copy number variance (CNV), determining species ratios, and determining methylation levels as in the example described above.

The quantitation method utilizes the specific PCR efficiency of the assay of interest and Ct values to calculate the relative percentage of one of the two states of a specific location or the relative abundance of the two targets in a sample.

Figure 1:
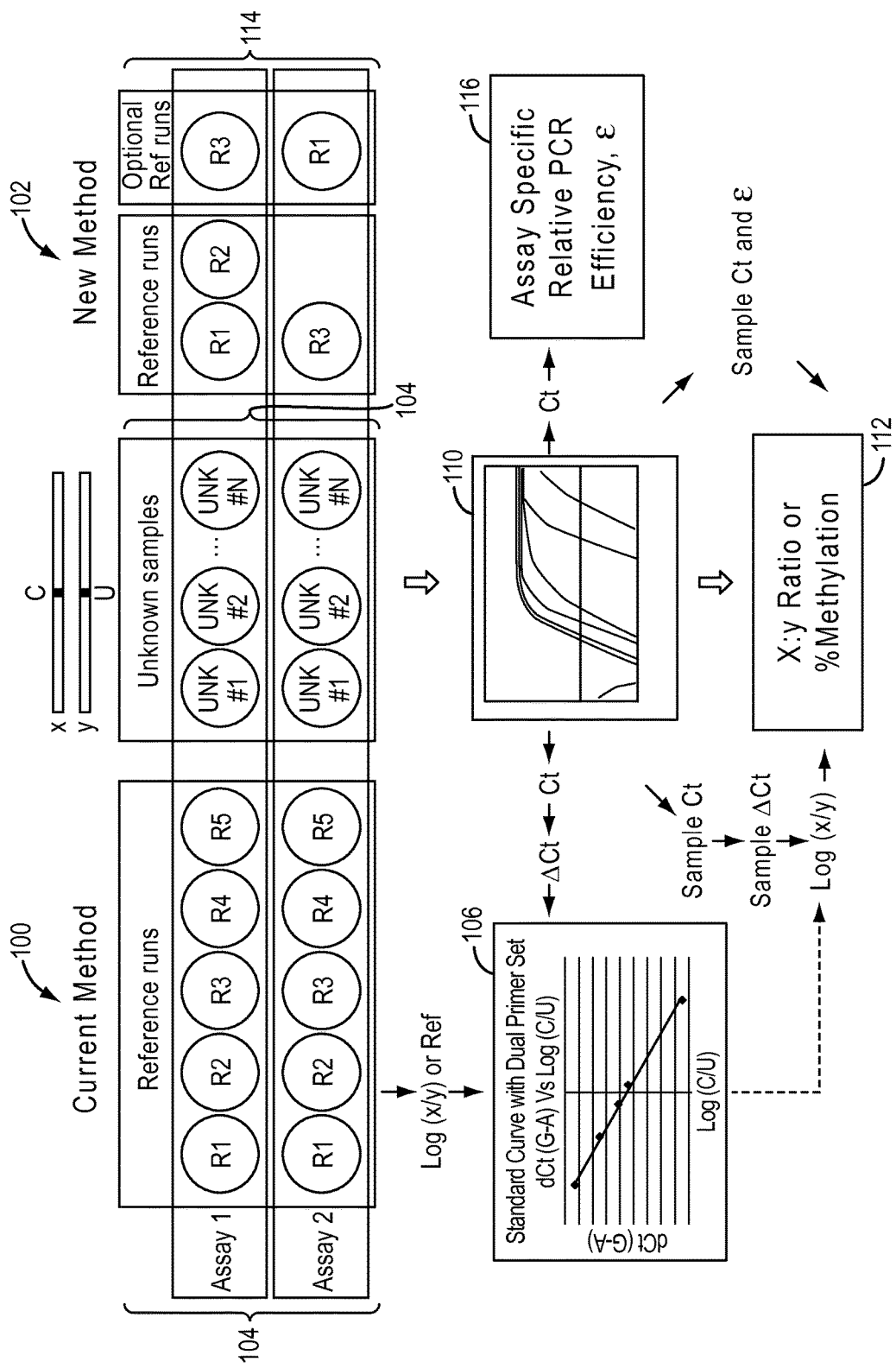
FIG. 1 illustrates a workflow comparing current quantitation methods and quantitation methods according to various embodiments described herein.

With reference to FIG. 1, workflow 100 shows a current quantitation method using a standard curve. Workflow 102 shows the quantitation method according to various embodiments described herein. In workflow 100, reference samples 104 are run to determine a standard curve shown in plot 106. The unknown samples are then amplified to generate amplification curves shown in plot 110. A Ct value may be determined from plot 110 for the unknown samples. ΔCt for the samples are determined and the standard curve is used to determine a x/y ratio result 112.

In comparison, workflow 102 illustrates the quantitation method according to various embodiments described herein. As in workflow 100, reference samples 114 are amplified. However, since a standard curve does not need to be generated, fewer reference samples 114 need to be run to determine a assay specific relative PCR efficiency, ε 116. Unknown samples 108 are amplified similarly to workflow 100 and a Ct for the sample is determined. Using the assay specific relative PCR efficiency, ε 116 and the Ct value, the x/y ratio result 112 is determined. As illustrated, workflow 102 is more simple and does not require as many reference samples to be run.

Using this quantitation method, according to various embodiment, in a methylation level measurement example, the two states are "C" for methylated strand after bisulfite conversion or "U" for unmethylated strand after bisulfite conversion. For Genotyping, the two states are SNP1 and SNP2. For CNV (Copy Number Variance), the two targets are the reference gene and the target gene. Assay can be designed with a single set of primer, specific to either state of strand; or dual set of primers, specific to both states of the strands or the targets in the sample.

For Methylation level measurement and Genotyping, the specific PCR efficiency of the assay(s) are determined by using two reference points. The reference samples may be, for example, 10% C/90% U and 100% C for a single primer assay. In another example, three reference points are used. The reference samples are 100% S1 control, 10% S1/90% S2 and 100% S2 control samples for a dual primer assay design, where S1 and S2 are the control samples with specific states. For Methylation level measurement, S1 can be 100% methylated control sample and S2 can be 100% unmethylated control sample. For Genotyping, S1 can be homozygous SNP1 and S2 can be homozygous SNP2. For CNV assay, the PCR efficiencies of the assays are determined by the reference samples of known ratio of Reference to Target gene copies.

Examples of other assay types and reference samples for various applications where the method according to various embodiments described herein can be found in table 1700 of FIG. 17.

For methylation level measurement, the specific PCR efficiency of one of the assays, S1A1, is determined by the equation $$\varepsilon = 10^{\left(\frac{1}{\Delta CT}\right)} \text{ where } \Delta CT = CT_{10\%A1} - CT_{100\%A1}.$$

For the second assay S2A2, the relative PCR efficiency is calculated as $$\varepsilon_{S2A2} = \varepsilon_{S1A1}^{\frac{CT_{100\%S1A1}}{CT_{100\%S2A2}}}.$$

Figure 19:
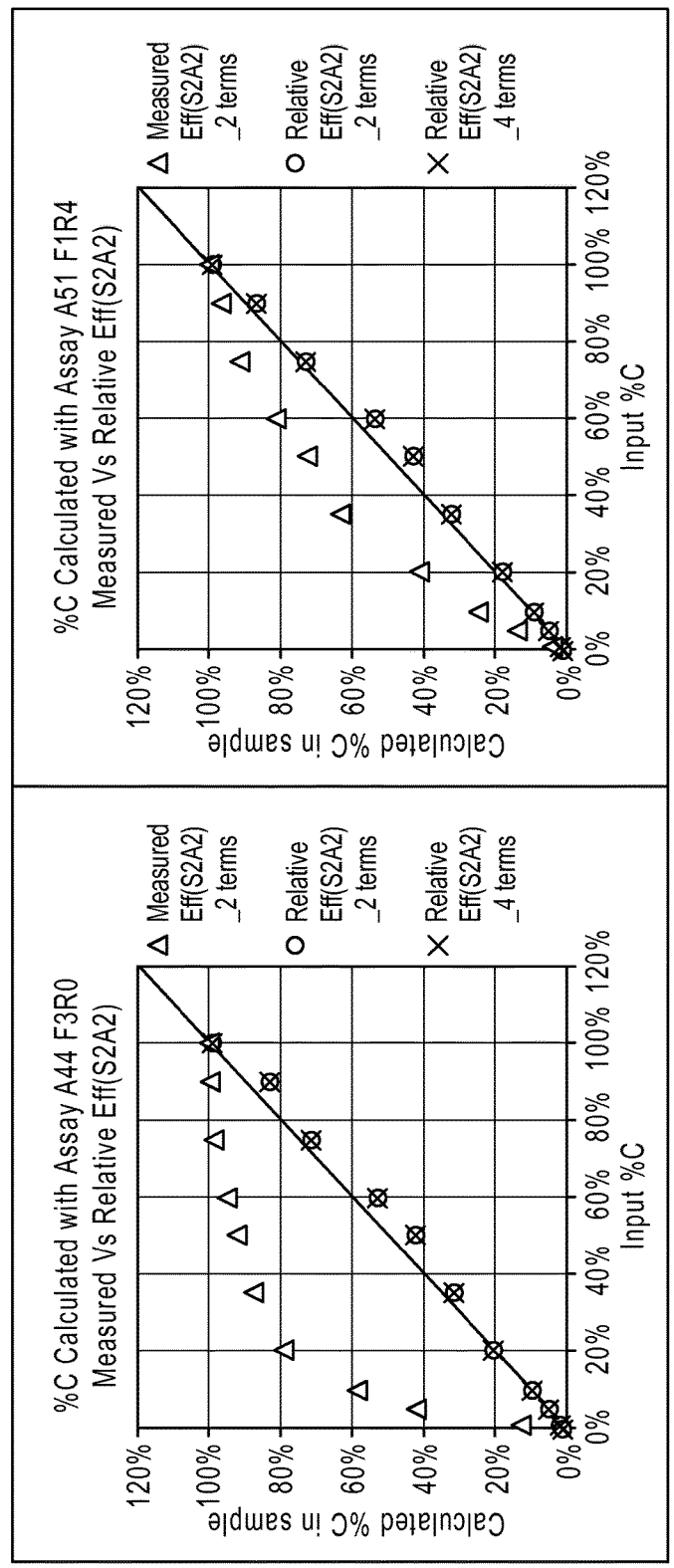
FIG. 19 illustrates the impact of using relative Eff(S2A2) on accuracy of quantitation. The table shows the values of Eff determined by different methods (measure Vs relative).

The use of relative PCR efficiency for S2A2 improves the accuracy of relative quantitation and allows the use of assays with different efficiencies in relative quantitation. Using the relative PCR efficiency, according to various embodiments described herein, eliminates the need of using assays of matching performances (similar efficiencies and Ct). Thus, virtually any assay may be used using the quantitation method according to various embodiments of the present teachings. FIG. 19 illustrates the impact of using relative Eff(S2A2) on accuracy of quantitation. The table shows the values of Eff determined by different methods (measure Vs relative).

For CNV and Genotyping, PCR efficiency of S1A1 (CNV: A1=Reference assay, S1=Reference gene; Genotyping: A1=SNP assay, S1=SNP1) is assumed to be 2.0 as most of the Reference Assays are optimized. For CNV, the PCR efficiency of S2A2 (A2=Target assay, S2=Target gene) is calculated from the Reference samples with known copy numbers for both Reference gene (X) and Target gene (Y). For Genotyping, the PCR efficiency of S2A2 (A2=SNP2 assay, S2=SNP2) can be calculated from the Reference samples with Homozygous SNP1, Homozygous SNP2 and heterozygous SNP1/SNP2.

The Principal

Figure 2:
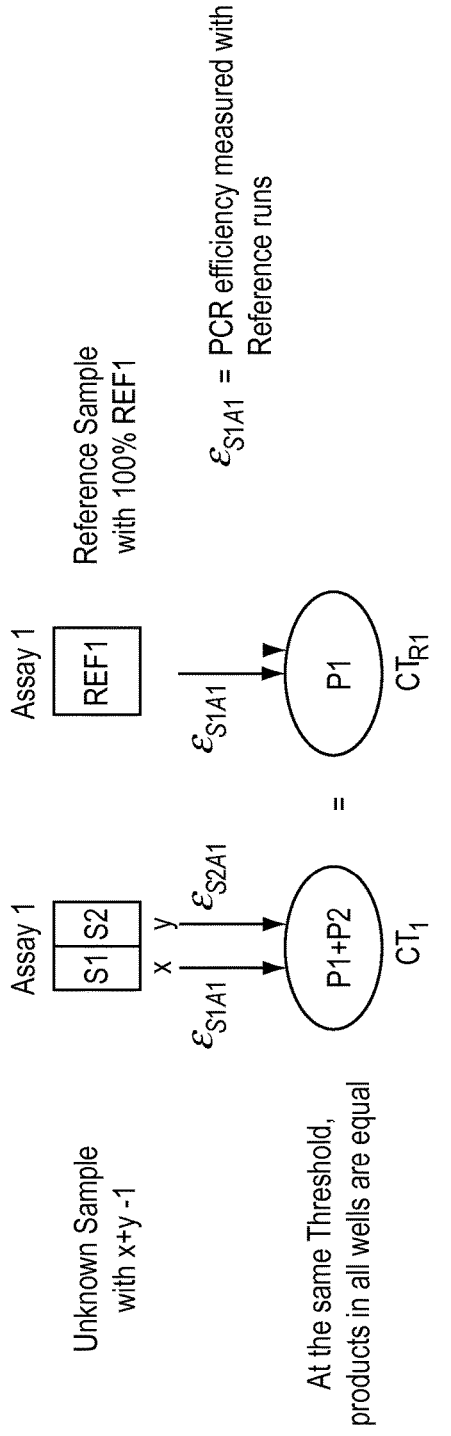
FIG. 2 illustrates a method of quantitation according to various embodiments described herein.

With reference to FIG. 2, according to various embodiments, a method for single Primer assay design (Sample=S1 and S2, Primer designed for Assay 1) is illustrated.

For a sample with two states (S1 and S2 at x:y ratio) at the location of assay, two reactions, S1-A1 and S2-A2, occur simultaneously. With the same amount of input template(s), at the same threshold, the product generated from the 100% S1 reference (REF1) is equivalent to the product generated from the sample.

At the same threshold, $$P_{R1} = P_1 + P_2$$

Where R1=100% S1 reference, x=% of S1 in sample and y=% of S2 in sample where x+y=1.

By definition, the amount of product can be expressed as $\varepsilon^{CT}$.

Substituting terms $$x\varepsilon_{S1A1}^{CT_1} + y\varepsilon_{S2A1}^{CT_1} = \varepsilon_{S1A1}^{CT_{R1}}$$

$$x\varepsilon_{S1A1}^{CT_1} + (1-x)\varepsilon_{S2A1}^{CT_1} = \varepsilon_{S1A1}^{CT_{R1}}$$

$$x\% = \left(\frac{\varepsilon_{S1A1}^{CT_{R1}} - \varepsilon_{S2A1}^{CT_1}}{\varepsilon_{S1A1}^{CT_1} - \varepsilon_{S2A1}^{CT_1}}\right) \times 100\%$$

For assays with good specificity, $\varepsilon_{S2A1} \ll \varepsilon_{S1A1}$ and $\varepsilon_{S2A1}^{CT_1}$ can be ignored. The equation can be simplified as $$x\% \approx \varepsilon_{S1A1}^{(CT_{R1}-CT_1)} \times 100\%$$

Dual Primer Assay Design (Sample=S1 and S2, Assay=A1 and A2)

Figure 3:
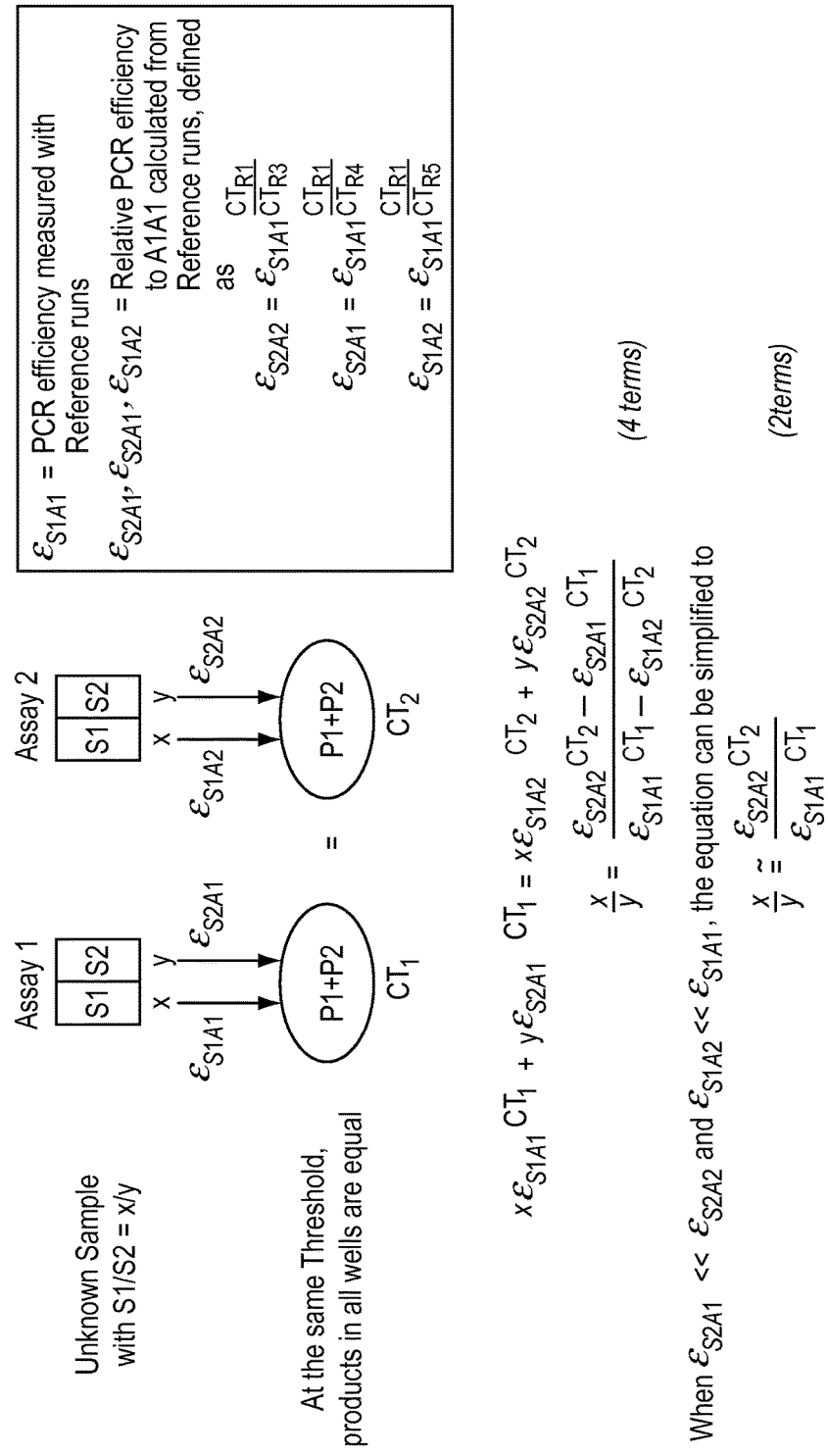
FIG. 3 illustrates a method of quantitation according to various embodiments described herein.

A method of a duel primer assay design according to various embodiments, is illustrated in FIG. 3, for example. With dual primer assay design, 4 reactions occur simultaneously. Applying the same principal, at the same threshold, products generated in different reaction wells are equal.

At the same threshold, $$P = P_1 + P_2 \text{ with both assays}$$

Amount of products can be expressed as $P = m\varepsilon^{CT}$ where P=product, m=amount of starting strands and $\varepsilon$=PCR efficiency Therefore, for Assay 1

$$P1 = x\varepsilon_{S1A1}^{CT_1}, P2 = y\varepsilon_{S2A1}^{CT_1}$$

And for Assay 2, $$P1 = x\varepsilon_{S1A2}^{CT_2}, P2 = y\varepsilon_{S2A2}^{CT_2}$$

Substituting terms $$x\varepsilon_{S1A1}^{CT_1} + y\varepsilon_{S2A1}^{CT_1} = x\varepsilon_{S1A2}^{CT_2} + y\varepsilon_{S2A2}^{CT_2}$$

$$\frac{x}{y} = \frac{\varepsilon_{S2A2}^{CT_2} - \varepsilon_{S2A1}^{CT_1}}{\varepsilon_{S1A1}^{CT_1} - \varepsilon_{S1A2}^{CT_2}}$$

If the specificity of the assay is very good, efficiencies for mismatched reactions are significantly lower than the matched reactions, $\varepsilon_{S1A2} \ll \varepsilon_{S1A1}$ and $\varepsilon_{S2A1} \ll \varepsilon_{S2A2}$. Terms $\varepsilon_{S2A1}^{CT_1}$ and $\varepsilon_{S1A2}^{CT_2}$ can be ignored. The equations can then be simplified as $$\frac{x}{y} \approx \frac{\varepsilon_{S2A2}^{CT_2}}{\varepsilon_{S1A1}^{CT_1}}$$

For Methylation level measurement, the sum of % methylated strand (x) and % unmethylated strand (y)=100%. To calculate % methylation (x) in the sample, rewrite the equation as $$R = \frac{x}{y} = \frac{x}{1-x}$$

$$x = \frac{R}{1+R}$$

For CNV, the PCR efficiency of S2A2 is determined from the Reference Samples with known copy numbers of both Reference. For each sample, X=Known Copy number of Reference gene and Y=Unknown Copy number of Target gene in the sample. The ratio between Reference gene to Target gene=x/y. Applying the equation:

$$\frac{x}{y} = R = \frac{\varepsilon_{S2A2}^{CT_2}}{\varepsilon_{S1A1}^{CT_1}}$$

where R=ratio of Reference gene to Target gene.

Rearranging the equation, $$R(\varepsilon_{S1A1}{}^{CT_1}) = \varepsilon_{S2A2}{}^{CT_2}$$

$$\log[R(\varepsilon_{S1A1}{}^{CT_1})] = CT_2(\log \varepsilon_{S2A2})$$

$\varepsilon_{S2A2}$ can be expressed as $$\varepsilon_{S2A2} = 10^{\frac{\log\left[R\left(\varepsilon_{S1A1}^{CT_1}\right)\right]}{CT_2}}$$

As the copy numbers of Reference gene (X) and Target gene (Y) in the Reference samples are known, R is known. With $\varepsilon_{S1A1}$ assumed to be 2.0, $\varepsilon_{S2A2}$ can be calculated for each Reference Sample. If multiple Reference Samples with different x/y ratio is used, the average $\varepsilon_{S2A2}$ is used.

In the sample where T=sum of copy number of Reference gene and copy number of Target gene, x=X/T and y=Y/T.

$$T = x + y \text{ and } x = \frac{R}{1+R}$$

As X is a known value, T can be calculated as

T=x/Known Copy Number of Reference Gene

Therefore,

Y=T-X

For Genotyping, x=% SNP1 and y=% SNP2. $\varepsilon_{S2A2}$ can be calculated as $$\varepsilon_{S2A2} = \varepsilon_{S1A1}^{\frac{CT_{100\%S1A1}}{CT_{100\%S2A2}}}$$

with two Reference Samples of homozygous SNP1 and homozygous SNP2 with $\varepsilon_{S1A1}$ assumed to be 2.0. If a Reference Sample is heterozygous SNP1/SNP2, $\varepsilon_{S2A2}$ can be calculated as $$\varepsilon_{S2A2} = 10^{\frac{\log\left[R\left(\varepsilon_{S1A1}^{CT_1}\right)\right]}{CT_2}}$$

where R=1 and $\varepsilon_{S1A1}$ assumed to be 2.0.

The genotype of the sample can be determined from the ratio (R=x/y) with the equations $$\frac{x}{y} \approx \frac{\varepsilon_{S2A2}^{CT_2}}{\varepsilon_{S1A1}^{CT_1}} \text{ and } x = \frac{R}{1+R}.$$

Example 1

In this section, examples of experiments using the quantitation method according to various embodiments are described.

In this example, the Assay and Primer=targeted 4 cancer promoter regions, each with different primer sequences as follows:

| Assay | Template |
|---|---|
| A02F0R0 | AGAATTGAGGGTGGTATAGAAGCGGGTAAAGGGGCGATCG GATTCGAGTTTAGGGAGGCGTATATAGGGGGCGTCGAGGT TCGAGAAGG (SEQ ID NO: 1) |
| A02F0R2 | AGAATTGAGGGTGGTATAGAAGCGGGTAAAGGGGCGATCG GATTCGAGTTTAGGGAGGCGTATATAGGGGGCGTCGAGGT TCGAGAAGG (SEQ ID NO: 1) |
| A44F3R0 | GCGAGGGAGAAATCGGTCGTTTTTTTTCGAAAGGTCGAAG TCGAGAGAAATAATTGATTTCGATAGGTTTGTTTCGTTTA GTTTTTGATAGTGAGGGG (SEQ ID NO: 2) |
| A44F3R2 | GCGAGGGAGAAATCGGTCGTTTTTTTTCGAAAGGTCGAAG TCGAGAGAAATAATTGATTTCGATAGGTTTGTTTCGTTTA GTTTTTGATAGTGAGGGG (SEQ ID NO: 2) |
| A51F1R1 | CGGGTAGGGATGTTTTTGCGTTTTCGGGCGGTTTCGGGTT TAGTTATTTGTTCGTCGGGGAAGGTAGG TTC (SEQ ID NO: 3) |
| A51F1R4 | CGGGTAGGGATGTTTTTGCGTTTTCGGGCGGTTTCGGGTT TAGTTATTTGTTCGTCGGGGAAGGTAGG TTC (SEQ ID NO: 3) |
| A54F0R2 | GGTAGATTGAGGGCGGTCGGGGAGTGAGGAGTCGCGGGGA GAGAGTCGCGGCGTTTTCGGGATAATGCGGCGGCGGTTTG TTTAGGTGGGGCGCGTGCGGTTATTT (SEQ ID NO: 4) |
| A54F2R5 | GGTAGATTGAGGGCGGTCGGGGAGTGAGGAGTCGCGGGGA GAGAGTCGCGCGTTTTCGGGATAATGCGGCGGCGGTTTG TTTAGGTGGGGCGCGTGCGGTTATTT (SEQ ID NO: 4) |

Master Mix=SYBR®Select Master Mix

Sample=Synthetic Templates

Assay 1=Primer G, Assay 2=Primer A

| Template ID | Synthetic Template Sequence |
|---|---|
| A51_AIIC | CGGGTAGGGATGTTTTTGCGTTTTCGGGCGGTTTCGG GTTTAGTTATTTGTTCGTCGGGGAAGGTAGGTTC (SEQ ID NO: 3) |
| A51_AIIU | UGGGTAGGGATGTTTTTGUGTTTTUGGGUGGTTTUGG GTTTAGTTATTTGTTUGTUGGGGAAGGTAGGTTC (SEQ ID NO: 5) |
| A54_AIIC | GGTAGATTGAGGGCGGTCGGGGAGTGAGGAGTCGCGG GGAGAGAGTCGCGGCGTTTTCGGGATAATGCGGCGGC GGTTTGTTTAGGTGGGGCGCGTGCGGTTATTT (SEQ ID NO: 4) |
| A54_AIIU | GGTAGATTGAGGGUGGTUGGGGAGTGAGGAGTUGUGG GGAGAGAGTUGUGGUGTTTTUGGGATAATGUGGUGGU GGTTTGTTTAGGTGGGGUGUGTGUGGTTATTT (SEQ ID NO: 6) |
| A02_AIIC | AGAATTGAGGGTGGTATAGAAGCGGGTAAAGGGGCGA TCGGATTCGAGTTTAGGGAGGCGTATATAGGGGGCGT CGAGGTTCGAGAAGG (SEQ ID NO: 1) |
| A02_AIU | AGAATTGAGGGTGGTATAGAAGUGGGTAAAGGGGUGA TUGGATTUGAGTTTAGGGAGGUGTATATAGGGGGUGT UGAGGTTUGAAGG (SEQ ID NO: 7) |
| A44_AIIC | GCGAGGGAGAAATCGGTCGTTTTTTTTCGAAAGGTCG AAGTCGAGAGAAATAATTGATTTCGATAGGTTTGTTT CGTTTAGTTTTTGATAGTGAGGGG (SEQ ID NO: 2) |

-continued

| Template ID | Synthetic Template Sequence |
|---|---|
| A44_AIIU | GUGAGGGAGAAATUGGTUGTTTTTTTTUGAAAGGTUG AAGTUGAGAGAAATAATTGATTTUGATAGGTTTGTTT UGTTTAGTTTTTGATAGTGAGGGG (SEQ ID NO: 8) |

To generate samples of various methylation levels, the AllC and AllU templates were mixed at specific ratios. 12 levels of methylation states were generated: 100%, 99%, 90%, 75%, 60%, 50%, 35%, 20%, 10%, 5%, 1% and 0%.

An exemplary plate layout is illustrated in FIG. 4.

Replicates=2 technical replicates. 10 uL reaction mix per well.

Run condition=Assay plate was run on Vii7 using standard PCR method for 40 cycles. PCR condition=s: 95° C. (2 minutes) followed by 40 cycles of 95° C. (15 seconds)–60° C. (1 minute) on ViiA7.

Threshold was set to 0.15 for all wells in this run.

Average CT of the 2 replicates was used in calculation.

Calculations

In this set of experimental values, the accuracy of the quantification method with Single and Dual primer assay designs according to various embodiments were compared with conventional method with standard curves.

Single Primer Assay Design

Calculation Using Standard Curve

Figure 5:
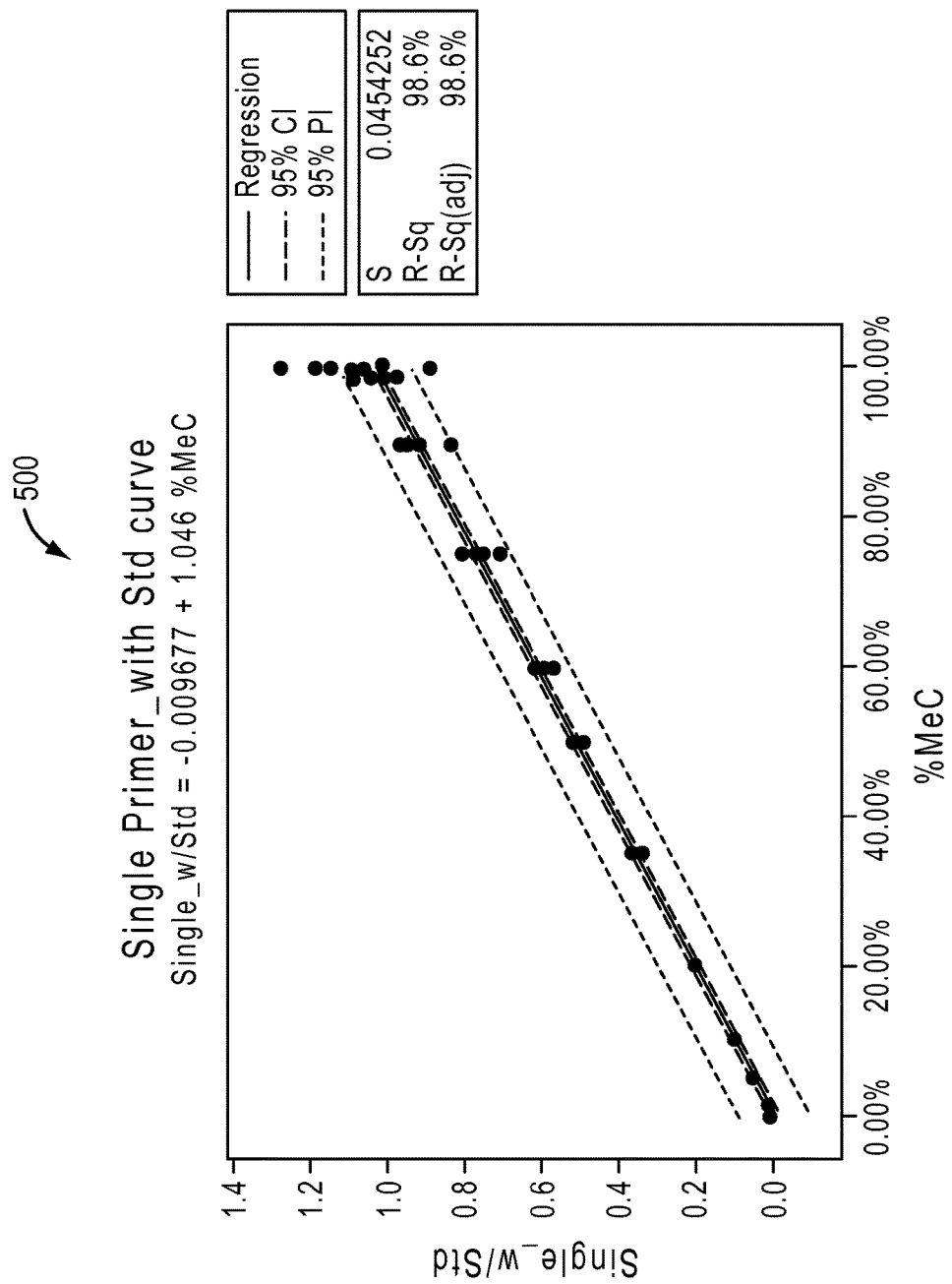
FIG. 5 illustrates an exemplary scattered plot of calculated % C using a traditional standard curve Vs. Input % C.

For comparison purpose, the 12 samples at different methylation levels were divided to 2 groups: Standards and Unknowns. A standard curve of CT Vs Log(% C) was generated with 6 data points (1%, 10%, 35%, 60% and 99%) of methylated samples. Slope and intercept of the standard curve were calculated from the data set and used to calculate the % C of the Unknowns were calculated using the slope and intercept from the standard curve. FIG. 5 illustrates scattered plot 500 of calculated % C using a standard curve Vs Input % C.

Calculation without Using a Standard Curve

Data points 10% and 100% methylated samples were used as Reference to calculated PCR efficiency of the specific assay using the equation $$\varepsilon = 10^{\left(\frac{1}{\Delta CT}\right)}$$

where $\Delta CT = CT_{10\%\ C} - CT_{100\%\ C}$.

Figure 6:
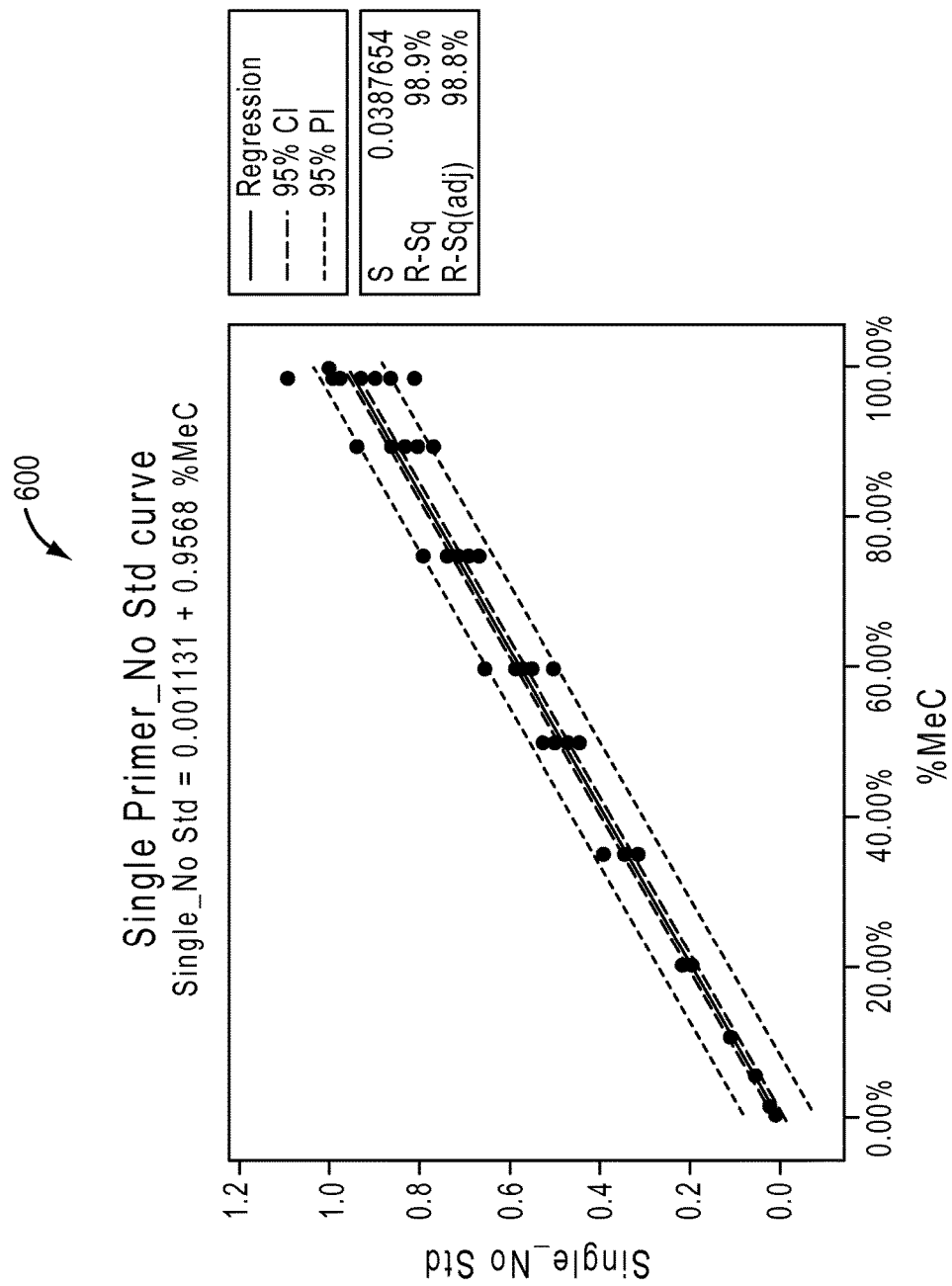
FIG. 6 illustrates an exemplary scattered plot of calculated % C not using standard curve Vs. Input % C according to various embodiments described herein.

% C of the other 10 samples were calculated with the equation $$x\% \approx \varepsilon_{S1A1}^{(CT_{R1}-CT_1)} \times 100\%$$

where % x=% C in this example, $CT_{R1}=CT_{100\%\ C}$ and $CT_1$=CT of unknown sample. FIG. 6 illustrates scattered plot 600 of calculated % C without standard curve Vs Input % C.

Dual Primer Assay Design

Calculation Using a Standard Curve—

Figure 7:
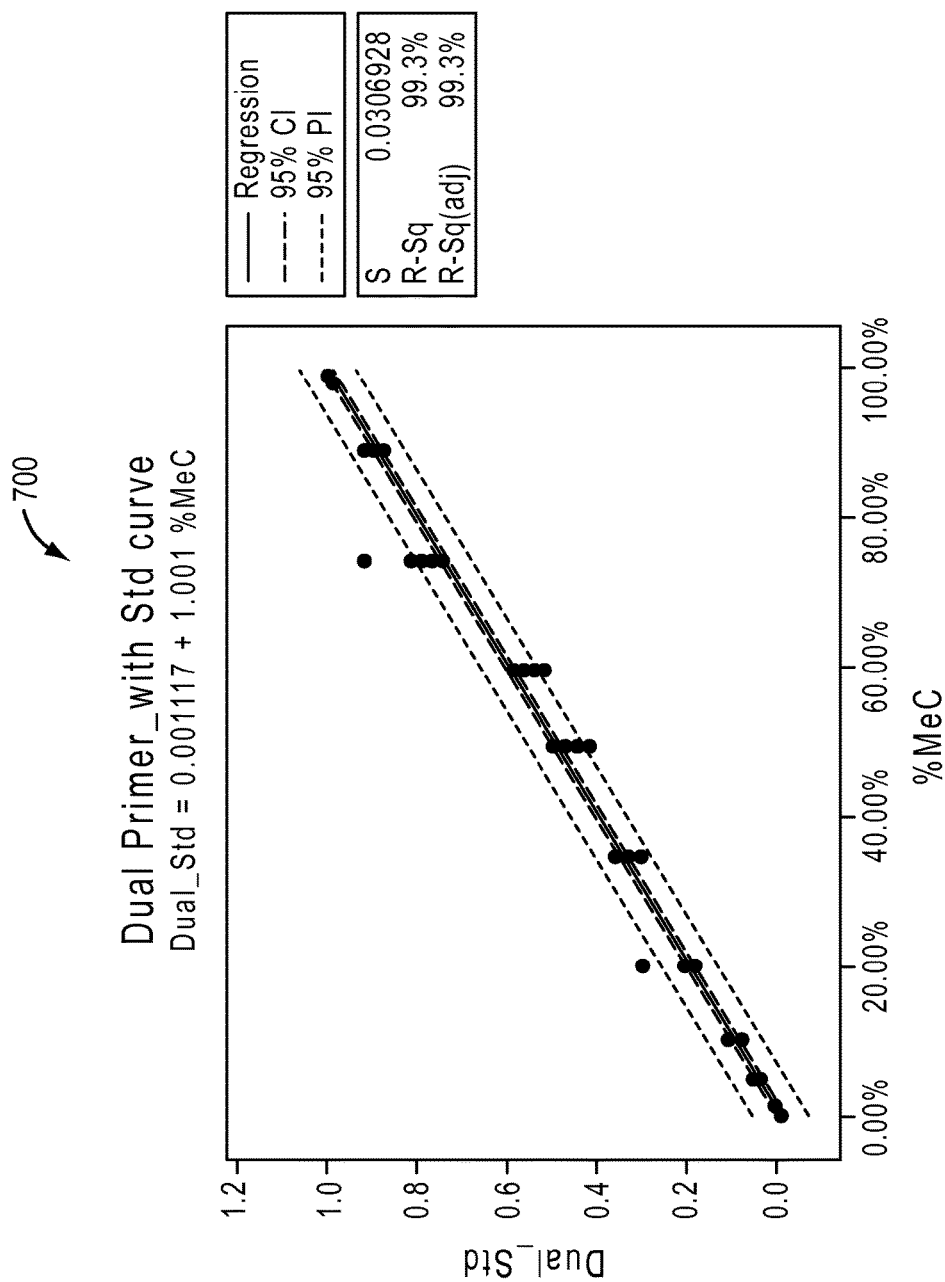
FIG. 7 illustrates another exemplary scattered plot of calculated % C using a traditional standard curve Vs. Input % C with Dual Primer Set with 8 assays.

For comparison purpose, the 12 samples at different methylation levels were divided to 2 groups: Standards and Unknowns. A standard curve of dCT Vs Log(% C/% U) was generated with 6 data points (1%, 10%, 35%, 60% and 99%) of methylated samples, where dCT=CT with Primer G–Ct with Primer A of each standard sample. Slope and intercept of the standard curve were calculated from the data set and used to calculate the % C of the Unknowns were calculated using the slope and intercept from the standard curve. FIG. 7 illustrates a scattered plot 700 of calculated % C with standard curve Vs Input % C with Dual Primer Set with 8 assays using a standard curve, according to various embodiments of the present teachings.

Calculation without Using a Standard Curve

Data for 10% and 100% methylated samples were used as Reference to calculate PCR efficiency of the specific (C-G) assay using the equation $$\varepsilon = 10^{\left(\frac{1}{\Delta CT}\right)}$$

where $\Delta CT = CT_{10\%\ C} - CT_{100\%\ C}$ with Primer Set G (Assay 1).

The % C/% U ratio of the other 10 samples were calculated with the equation $$\frac{x}{y} \approx \frac{\varepsilon_{S2A2}^{CT_2}}{\varepsilon_{S1A1}^{CT_1}}$$

Where, $\varepsilon_{S1A1}$=calculated PCR efficiency of C-G reaction $\varepsilon_{S2A2}$ = relative PCR efficiency of U-A reactions with reference to C-G reaction = $\varepsilon_{S1A1}^{\frac{CT_{100\%S1A1}}{CT_{100\%S2A2}}}$ where $CT_{100\%\ S1A1}$=CT of 100% C Standard with Primer G, and $CT_{100\%\ S2A2}$=CT of 0% C (100% U) Standard with Primer A % C of the Unknown samples was calculated from the x/y ratio (R) with the equation $$\%C = \frac{R}{1+R}$$

Figure 8:
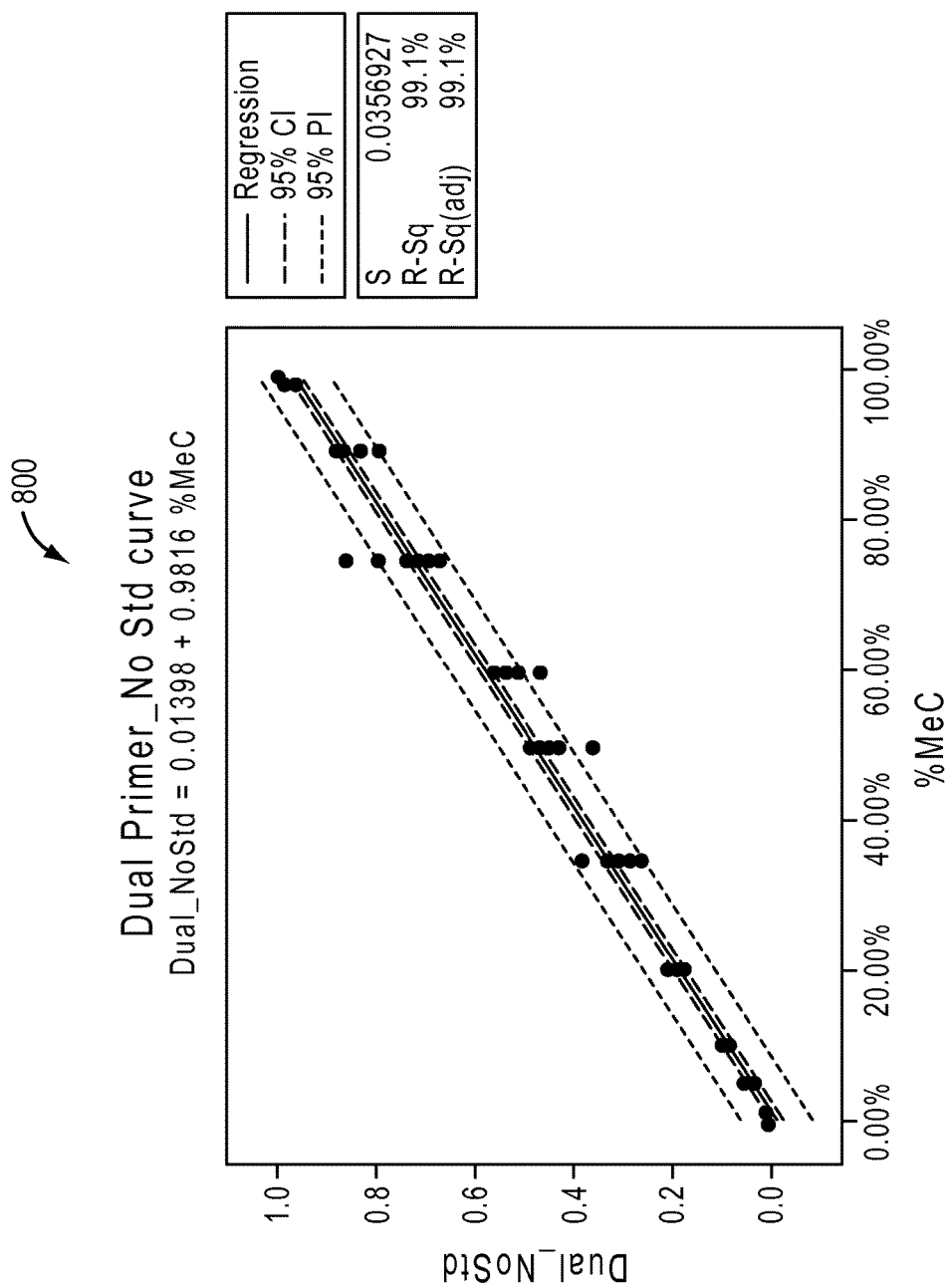
FIG. 8 illustrates another exemplary scattered plot of calculated % C not using a standard curve Vs. Input % C with Dual Primer Set with 8 assays, according to various embodiments of the present teachings.

FIG. 8 illustrates scattered plot of calculated % C without standard curve Vs Input % C with Dual Primer Set with 8 assays, according to various embodiments of the present teachings.

Example 2: Measuring % C in Bisulfite Converted gDNA Templates with Single Primer Set Experiment Design 6 Assays at 5 Cancer Promoter Regions Template DNA=0% and 100% Bisulfite converted gDNA from Qiagen. A series of samples at different % C level (0%, 5%, 10%, 15%, 40%, 70%, 90%, 100%) was generated by mixing the 0% and 100% gDNA. Samples with 10% and 100% C were used as Reference to calculate PCR efficiency.

Assay 1=G primer set

PCR condition=95 C (2 m)–[95 C (15 s)–60 C (1 m)]₄₀ on ViiA7

Figure 9:
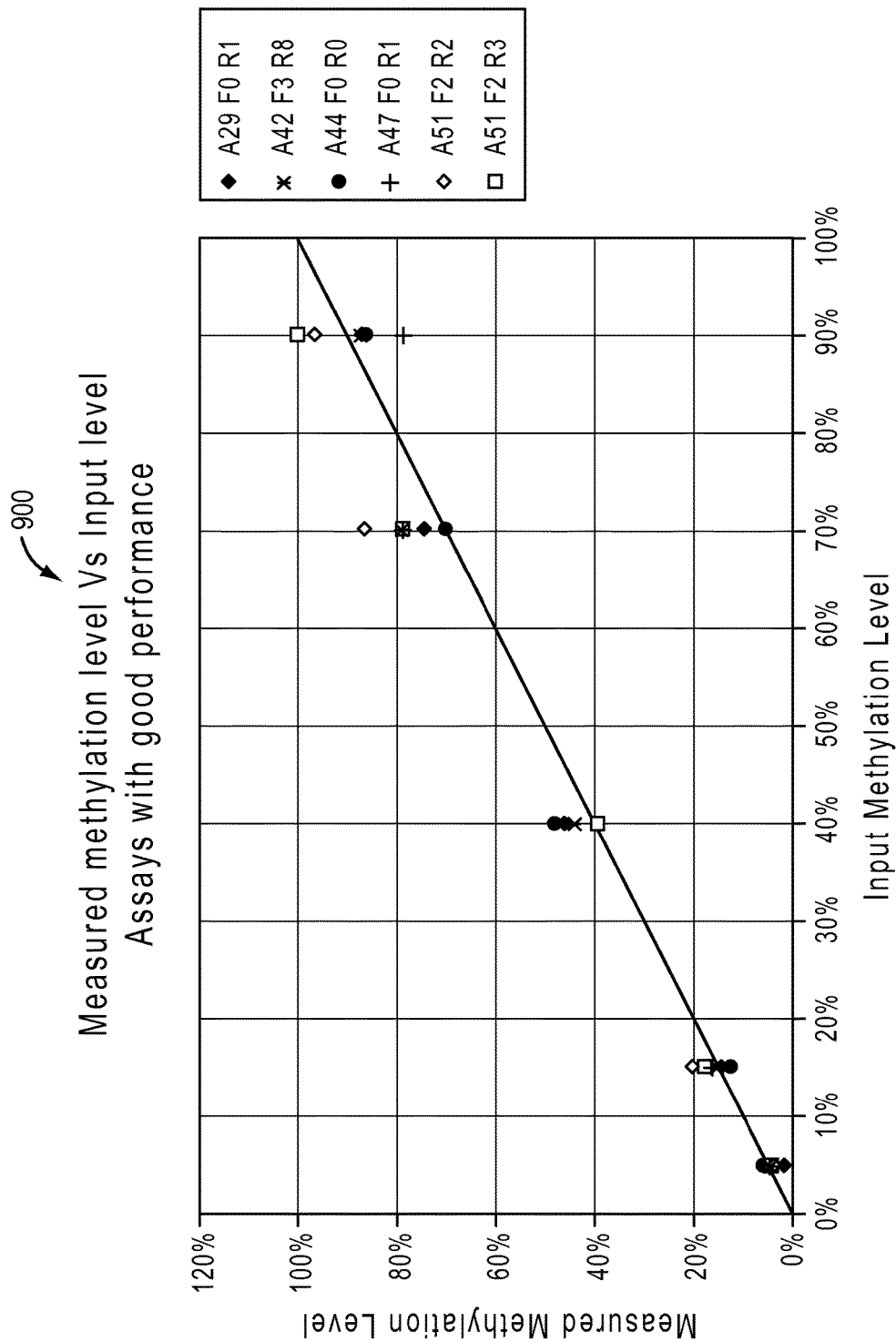
FIG. 9 illustrates measured methylation levels using the quantitation method vs. input methylation levels according to various embodiments described herein.

% C of samples were calculated using Single Primer Assay design without Standard Curve The results, according to various embodiments described herein are shown in FIG. 9. Scattered plot 900 shows measured % C Vs. Input % C.

Computer-Implemented System

Those skilled in the art will recognize that the operations of the various embodiments described herein may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on non-transitory computer-readable media. Some other processes can be implemented using analog circuitry, as is well known to one of ordinary skill in the art. Additionally, memory or other storage, as well as communication components, may be employed in embodiments of the invention.

Figure 10:
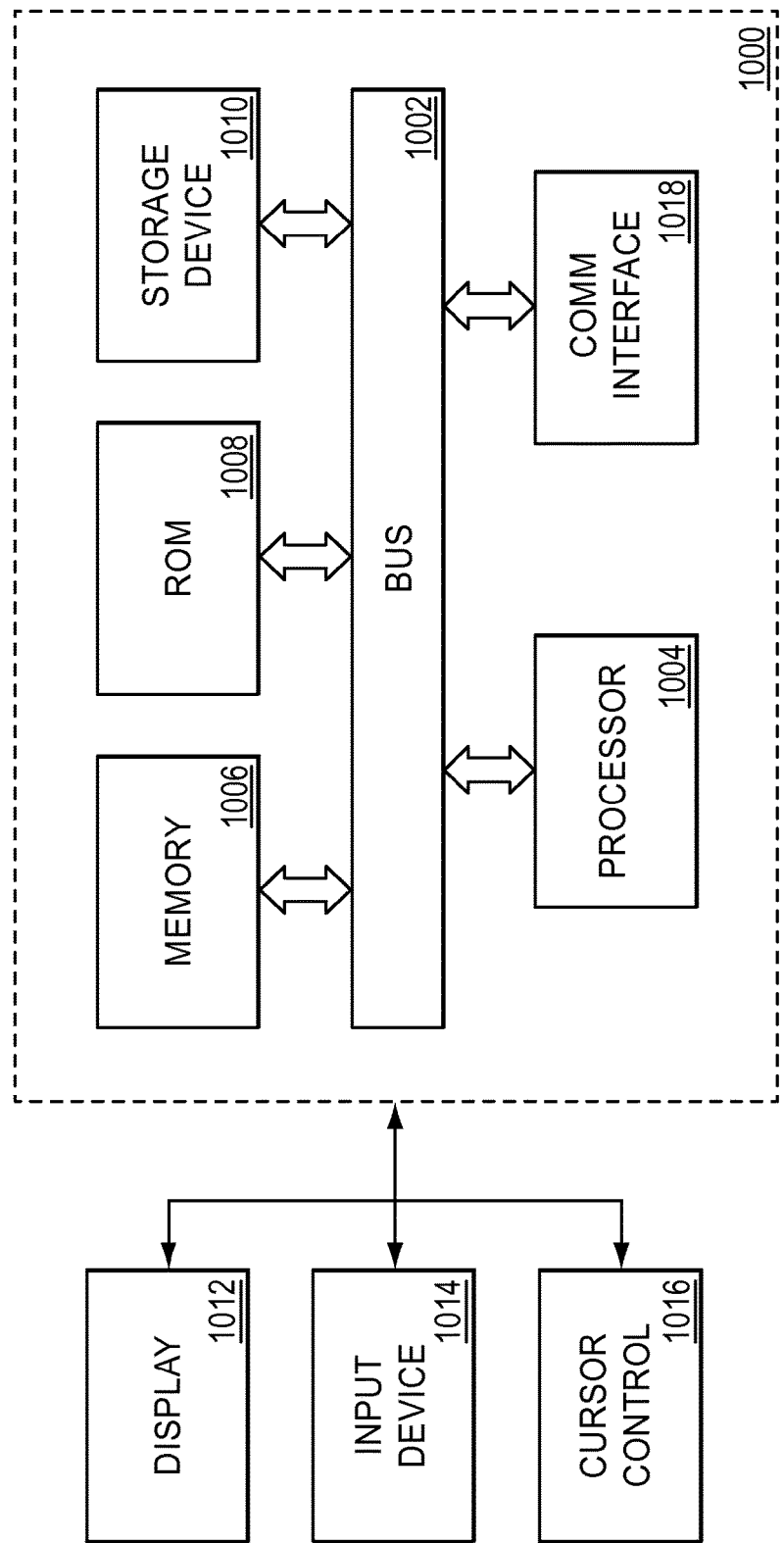
FIG. 10 illustrates an exemplary block diagram of a computing system for implementing the quantitation method according to various embodiments described herein.

FIG. 10 is a block diagram that illustrates a computer system 1000 that may be employed to carry out processing functionality, according to various embodiments. Instruments to perform experiments may be connected to the exemplary computing system 1000. Computing system 1000 can include one or more processors, such as a processor 1004. Processor 1004 can be implemented using a general or special purpose processing engine such as, for example, a microprocessor, controller or other control logic. In this example, processor 1004 is connected to a bus 1002 or other communication medium.

Further, it should be appreciated that a computing system 1000 of FIG. 10 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 1000 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art. According to various embodiments described herein, computing system 1000 may be configured to connect to one or more servers in a distributed network. Computing system 1000 may receive information or updates from the distributed network. Computing system 1000 may also transmit information to be stored within the distributed network that may be accessed by other clients connected to the distributed network.

Computing system 1000 may include bus 1002 or other communication mechanism for communicating information, and processor 1004 coupled with bus 1002 for processing information.

Computing system 1000 also includes a memory 1006, which can be a random access memory (RAM) or other dynamic memory, coupled to bus 1002 for storing instructions to be executed by processor 1004. Memory 1006 also may be used for storing temporary variables or other intermediate information during execution of instructions to be executed by processor 1004. Computing system 1000 further includes a read only memory (ROM) 1008 or other static storage device coupled to bus 1002 for storing static information and instructions for processor 1004.

Computing system 1000 may also include a storage device 1010, such as a magnetic disk, optical disk, or solid state drive (SSD) is provided and coupled to bus 1002 for storing information and instructions. Storage device 1010 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 1010 may include other similar instrumentalities for allowing computer programs or other instructions or data to be loaded into computing system 1000. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 1010 to computing system 1000.

Computing system 1000 can also include a communications interface 1018. Communications interface 1018 can be used to allow software and data to be transferred between computing system 1000 and external devices. Examples of communications interface 1018 can include a modem, a network interface (such as an Ethernet or other NIC card), a communications port (such as for example, a USB port, a RS-232C serial port), a PCMCIA slot and card, Bluetooth, etc. Software and data transferred via communications interface 1018 are in the form of signals which can be electronic, electromagnetic, optical or other signals capable of being received by communications interface 1018. These signals may be transmitted and received by communications interface 1018 via a channel such as a wireless medium, wire or cable, fiber optics, or other communications medium. Some examples of a channel include a phone line, a cellular phone link, an RF link, a network interface, a local or wide area network, and other communications channels.

Computing system 1000 may be coupled via bus 1002 to a display 1012, such as a cathode ray tube (CRT) or liquid crystal display (LCD), for displaying information to a computer user. An input device 1014, including alphanumeric and other keys, is coupled to bus 1002 for communicating information and command selections to processor 1004, for example. An input device may also be a display, such as an LCD display, configured with touchscreen input capabilities. Another type of user input device is cursor control 1016, such as a mouse, a trackball or cursor direction keys for communicating direction information and command selections to processor 1004 and for controlling cursor movement on display 1012. This input device typically has two degrees of freedom in two axes, a first axis (e.g., x) and a second axis (e.g., y), that allows the device to specify positions in a plane. A computing system 1000 provides data processing and provides a level of confidence for such data. Consistent with certain implementations of embodiments of the present teachings, data processing and confidence values are provided by computing system 1000 in response to processor 1004 executing one or more sequences of one or more instructions contained in memory 1006. Such instructions may be read into memory 1006 from another computer-readable medium, such as storage device 1010. Execution of the sequences of instructions contained in memory 1006 causes processor 1004 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 1004 for execution. Such instructions, generally referred to as "computer program code" (which may be grouped in the form of computer programs or other groupings), when executed, enable the computing system 1000 to perform features or functions of embodiments of the present invention. These and other forms of non-transitory computer-readable media may take many forms, including but not limited to, non-volatile media, volatile media, and transmission media. Non-volatile media includes, for example, solid state, optical or magnetic disks, such as storage device 1010. Volatile media includes dynamic memory, such as memory 1006. Transmission media includes coaxial cables, copper wire, and fiber optics, including the wires that comprise bus 1002.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 1004 for execution. For example, the instructions may initially be carried on magnetic disk of a remote computer. The remote computer can load the instructions into its dynamic memory and send the instructions over a telephone line using a modem. A modem local to computing system 1000 can receive the data on the telephone line and use an infra-red transmitter to convert the data to an infra-red signal. An infra-red detector coupled to bus 1002 can receive the data carried in the infra-red signal and place the data on bus 1002. Bus 1002 carries the data to memory 1006, from which processor 1004 retrieves and executes the instructions. The instructions received by memory 1006 may optionally be stored on storage device 1010 either before or after execution by processor 1004.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Example 3: Copy Number Determination: Copy Number of C4A, C4B, C4S and C4L

4 Target Assays (FAM) and 1 Reference Assay (VIC)

| |
|---|
| C4A Hs07226349_cn |
| C4B Hs07226350_cn |
| C4S Hs07226351_cn |
| C4L Hs07226352_cn |

Sample=gDNA with 33 Unknowns, 3 Calibrators (Reference) and 3 NTC. 10 ng gDNA per well. 4 Replicate runs per sample.

Master Mix=GT MMx

Thermocycling profile:

| Thermocycling Stage | Temp | Time | Cycles |
|---|---|---|---|
| Hot Start | 95 C. | 10 min | Hold |
| Denature | 95 C. | 15 sec | 40 cycles |
| Anneal/Extend | 60 C. | 1 min | |

For comparison purpose, analysis was done with Copy-Caller software v2.0. Copy number predicted with the software was generated for the samples.

Determining Copy Number for Target Gene in Sample

PCR Efficiency of Reference Assay (S1A1) is assumed to be 2.0.

PCR efficiency of the Target Assay (S2A2) was determined with $$\varepsilon_{S2A2} = 10^{-\frac{\log\left[R\left(\varepsilon_{S1A1}^{CT_1}\right)\right]}{CT_2}}$$

where R=Copy number of Ref gene/Copy of Target Gene in each reference sample. $CT_1$=CT of Reference sample at VIC channel. $CT_2$=CT of Reference sample at FAM channel. The average $\varepsilon_{S2A2}$ calculated from all three Reference samples was used for determination of copy numbers of Target genes in samples.

For the samples, Ratio (R=x/y) was determined with equation $$\frac{x}{y} \approx \frac{\varepsilon_{S2A2}^{CT_2}}{\varepsilon_{S1A1}^{CT_1}}$$

and x was calculated with equation $$x = \frac{R}{1+R}$$

where $CT_1$=CT of Sample at VIC channel and $CT_2$=CT of Sample at FAM channel. The copy number of the Reference gene (X)=2 and copy number of the Target gene in each sample is calculated as Y=X/x−X. The calculated copy number of Target gene in samples were compared with the Copy Number predicted by the CopyCaller.

Example 4: Determining Genotype in Sample

Assays=Standard Genotyping assays for SNP1 (FAM) and SNP2 (VIC)

Reference samples=Homozygous SNP1/SNP1 and Homozygous SNP2/SNP2 and/or Heterozygous SNP1/SNP2

Sample=gDNA samples with unknown genotype at target locus

Run plate on qPCR instrument with standard run protocol for 40 cycles. Collect real time data on instrument.

The PCR efficiency of SNP1 assay (S1A1) is assumed to be 2.0. Calculate the PCR efficiency of SNP2 assay, $\varepsilon_{S2A2}$ with the two homozygous reference samples, SNP1/SNP1 and SNP2/SNP2 with equation $$\varepsilon_{S2A2} = \varepsilon_{S1A1}^{\frac{CT_{100\%S1A1}}{CT_{100\%S2A2}}}$$

where $CT_{100\%\ S1A1}$=CT of SNP1/SNP1 at FAM channel and $CT_{100\%\ S2A2}$=CT of SNP2/SNP2 at VIC channel. Calculate the PCR efficiency for $\varepsilon_{S2A2}$ with $$\varepsilon_{S2A2} = 10^{\frac{\log\left[R\left(\varepsilon_{S1A1}^{CT_1}\right)\right]}{CT_2}}$$

where $CT_1$=CT of Heterozygous SNP1/SNP2 sample at FAM channel and $CT_2$=CT of Heterozygous SNP1/SNP2 sample at VIC channel. Calculate the average $\varepsilon_{S2A2}$.

Calculate the SNP1/SNP2 ratio for each sample using equation $$\frac{x}{y} \approx \frac{\varepsilon_{S2A2}^{CT_2}}{\varepsilon_{S1A1}^{CT_1}}$$

where $CT_1$=CT of sample at FAM channel and $CT_2$=CT of sample at VIC channel.

Determine x with $$x = \frac{R}{1+R}$$

where R=x/y. If x of the sample is approximately 1, the sample has genotype of SNP1/SNP1. If x the sample is approximately 0.5, the sample has genotype of SNP1/SNP2. If x of the sample is approximately 0, the sample has genotype of SNP2/SNP2.

Example 5

Understanding the changes in DNA methylation level provides important insight into gene regulation and cancer. Here we present a simple, accurate and cost effective quantitative method using SYBR® assay. By combining the high performance of SYBR® Select Master Mix and a new quantitation method, accurate methylation level was determined in a simple workflow with high flexibility without the need of standard curves. Consistent amplification and high specificity were found with 93% (128 of 138) assays designed with wide % GC (16-100%) range. The mean deviation of methylation level determined for bisulfate converted gDNA and synthetic templates was ≈4%. This work validated SYBR® Select Master Mix as an efficient and cost effective reagent for methylation assays. Although various embodiments have been described with respect to certain exemplary embodiments, examples, and applications, it will be apparent to those skilled in the art that various modifications and changes may be made without departing from the present teachings.

DNA methylation has strong association with regulation of gene expression, chromosomal stability and cell development. Change in methylation state can be used as biomarkers for early diagnosis, progression and prognosis of cancer as well as aging rate comparison and other applications. Numerous quantitative methods have been developed with various platforms to measure level of DNA methylation1, including qPCR with TaqMan® assays or SYBR® assays with standard curves.

Life Technologies' SYBR® Select Master Mix is a high performance master mix with high specificity and consistent amplification across a wide dynamic range. In this study, its potential as a cost effective option for methylation study was evaluated.

A new quantitation method has been developed to provide accurate quantitative measurement of change in methylation level without the generation of standard curve with SYBR® assays. The workflow and performance of this new method is compared with the conventional quantitation method with standard curves.

Experimental Design

Targets and Assay Design: 138 assays for 100% MeC strand were designed for 10 randomly selected cancer promoter regions without specific screening. The only criterion used in the assay design was to keep Tm around 60° C. As a result, assays with a wide range of GC contents (16-100%) and length (10-32 bp) were generated. The targets and assay properties are summarized in Table 1100 shown in FIG. 11. For quantitative measurements, a second assay was designed for 0% MeC strand.

Samples/Targets: EpiTect Control DNA, methylated (Qiagen) was used as 100% MeC gDNA and EpiTect Control DNA, unmethylated (Qiagen) was used as 0% MeC gDNA. Synthetic templates for 4 of the assays were ordered as Ultramers from IDT and pooled at 1:1 ratio. For quantitative measurements, 100% MeC and 0% MeC target sequences were mixed at various ratio to create samples with different methylation levels between 0%-100%. Primers: All primers used were synthesized in-house. Master Mix: A special version of SYBR® Select Master Mix without UDG was prepared for this study to avoid the digestion of dU in the bisulfite converted gDNA. PCR runs: All reactions were run in 384 well plates with 2 technical replicates for each reaction using the same thermal cycling conditions (FIG. 11) on ViiA™ 7 Real-Time PCR System (Applied Biosystems®). Each reaction started with 5 ng of gDNA or 0.04 fmol of synthetic template pools with 500 nM of each primer in 10 μL reaction volume per well.

Figure 12:
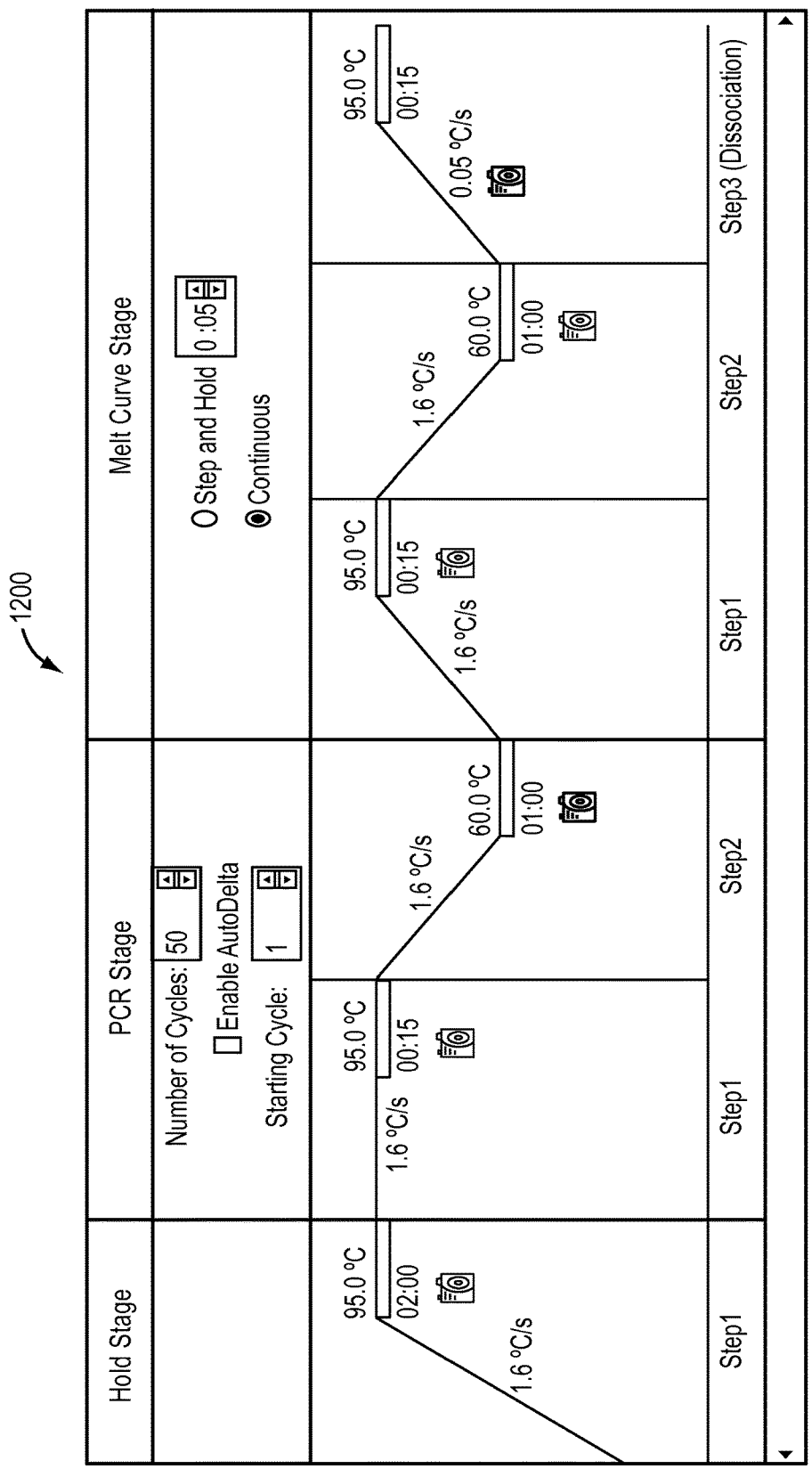
FIG. 12 illustrates an exemplary thermal profile used in experiments to generate data according to the quantitation method according to various embodiments described herein.

FIG. 12 illustrates the thermal profile used for all runs in this example.

Data Analysis: ViiA™ 7 software (Applied Biosystems®) was used for data analysis. Same threshold was used for the entire plate. Average CT of the technical replicates is used for all calculations.

Figure 13:
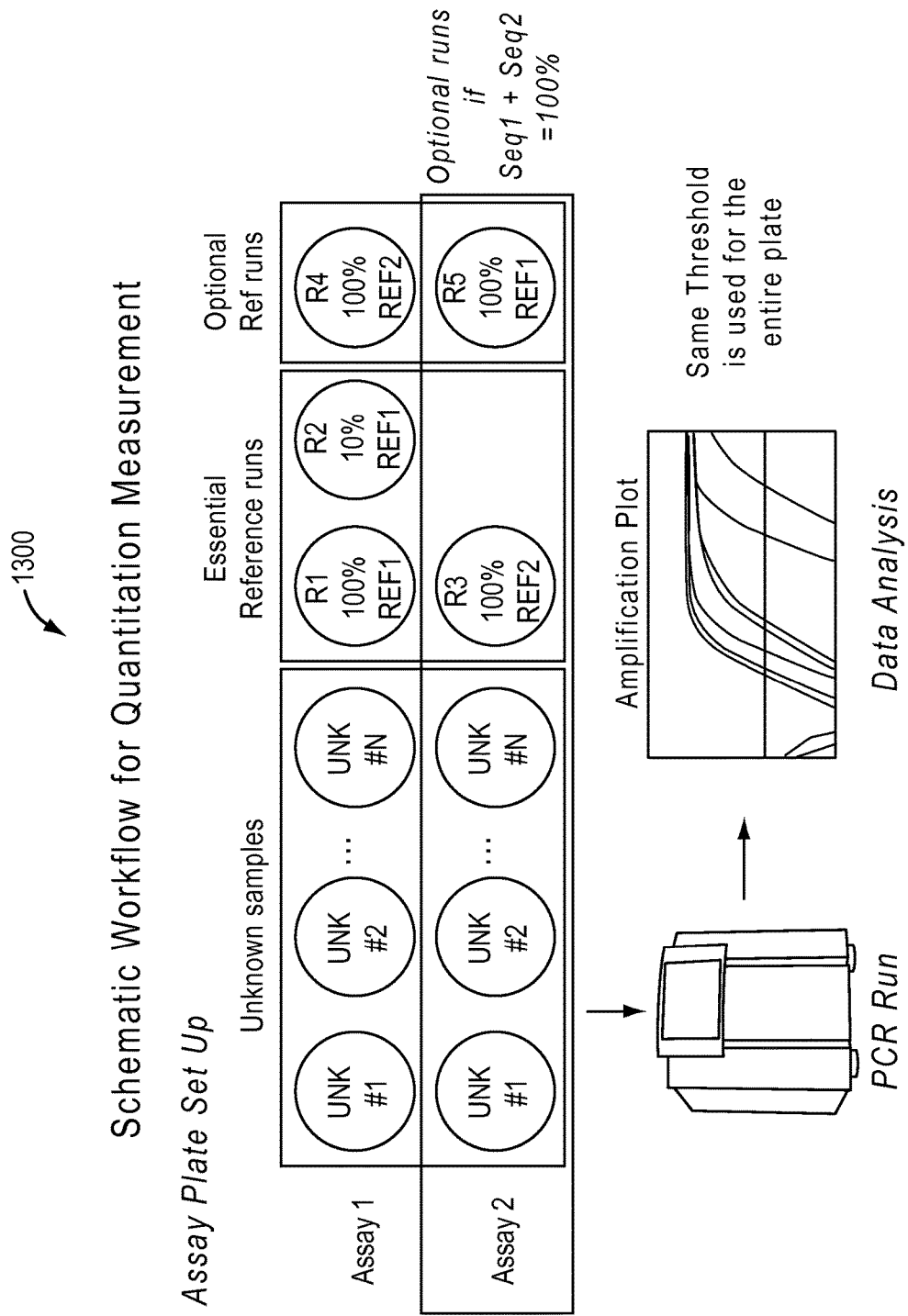
FIG. 13 illustrates an overview of the quantitation method according to various embodiments described herein.

FIG. 13 illustrates an overview schematic of the quantitation method used in this example, according to various embodiments of the present teachings.

Evaluation of Quantitation Method

% MeC of a set of samples was determined with the method(s) described and compared with the result determined with standard curves and the input level. Assay for 100% MeC is defined as Assay1 and assay for 0% MeC is defined as Assay2. Representative result with gDNA and synthetic template is presented in FIGS. 3a and 3b. Results demonstrated that it is essential to use relative PCR efficiency in the calculation. All methods based on relative PCR efficiency demonstrated excellent correlation with input % MeC and calculated % MeC with standard curves. Comparable results were obtained with the 3 options in the calculations (2-Assay (4 terms), 2-Assay (2 terms) and 1-Assay), with least bias found with 2-Assay (4 terms) method (FIG. 4). Mean deviation was defined as $\sqrt{[\Sigma(x-xi)2)/n]}$. Among the 4 gDNA assays, A51 was a poor performing assay with low PCR efficiency (measured $\varepsilon S1A1=1.55$ and measured $\varepsilon S2A2=4.4$). The mean deviation with A51 was <15% with 2 of the 3 options. With all other assays, the mean deviation with the 3 options was 3.7% with 2-Assay (4 terms), 4.4% with 2-Assay (2 terms) and 4.9% with 1-Assay method.

Figure 14A:
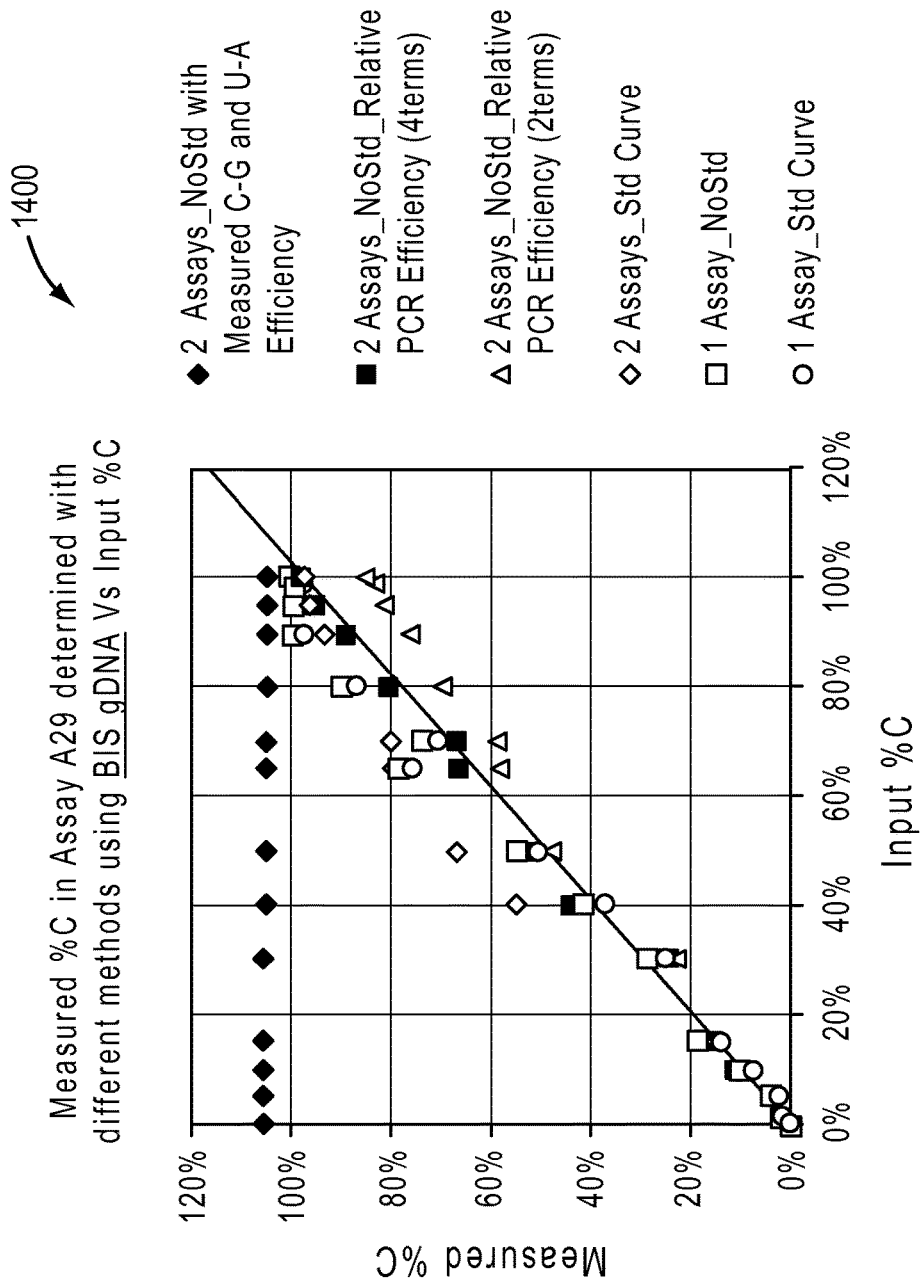
FIG. 14 illustrates plots of quantitation results with (a) bisulfite converted gDNA and (b) synthetic templates according to various embodiments described herein.
Figure 14B:
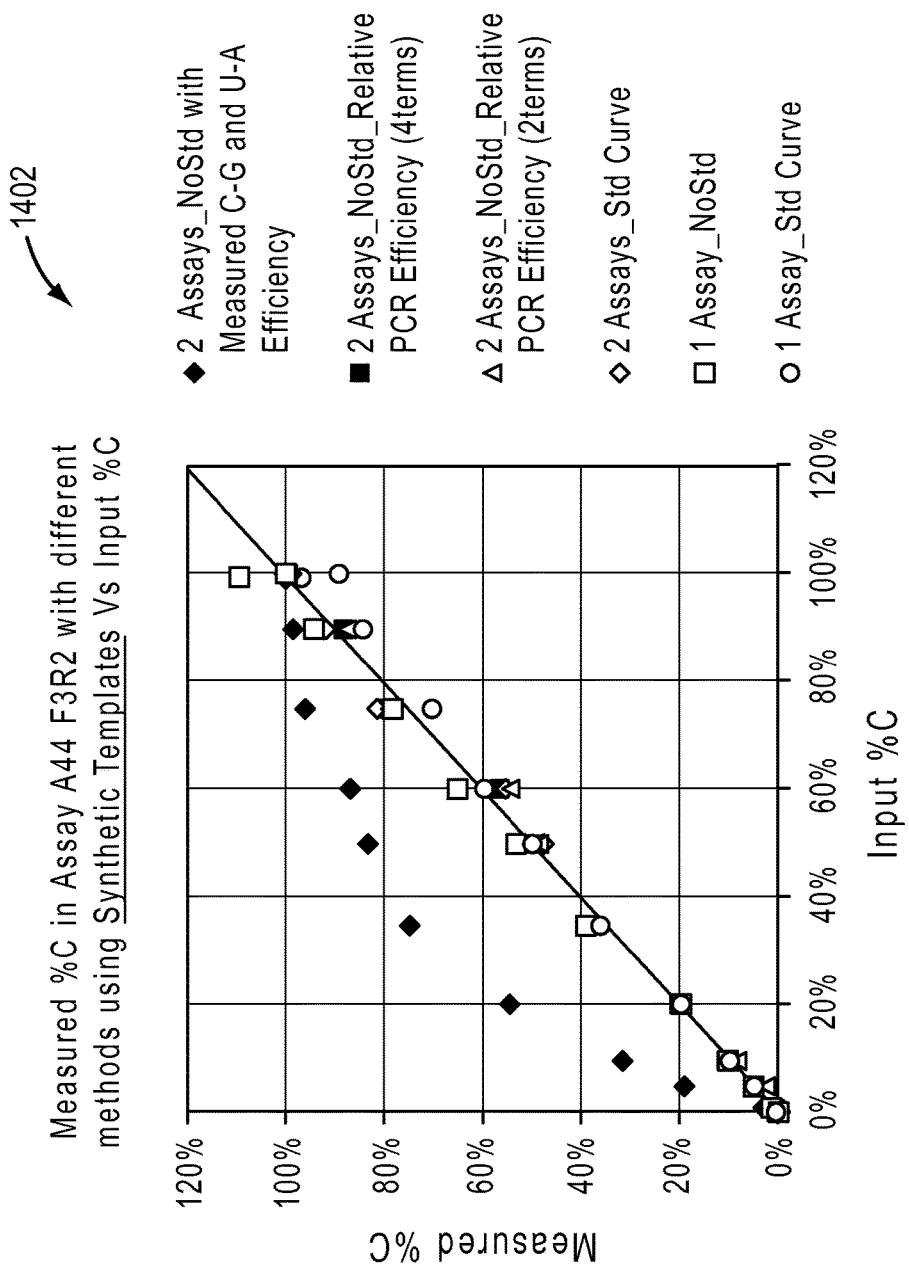

FIG. 14 shows a representative quantitation result with (a) bisulfite converted gDNA and (b) synthetic templates. This data illustrates the impacting of using relative efficiency (plot 1400) versus calibrated efficiency (plot 1402).

Figure 15:
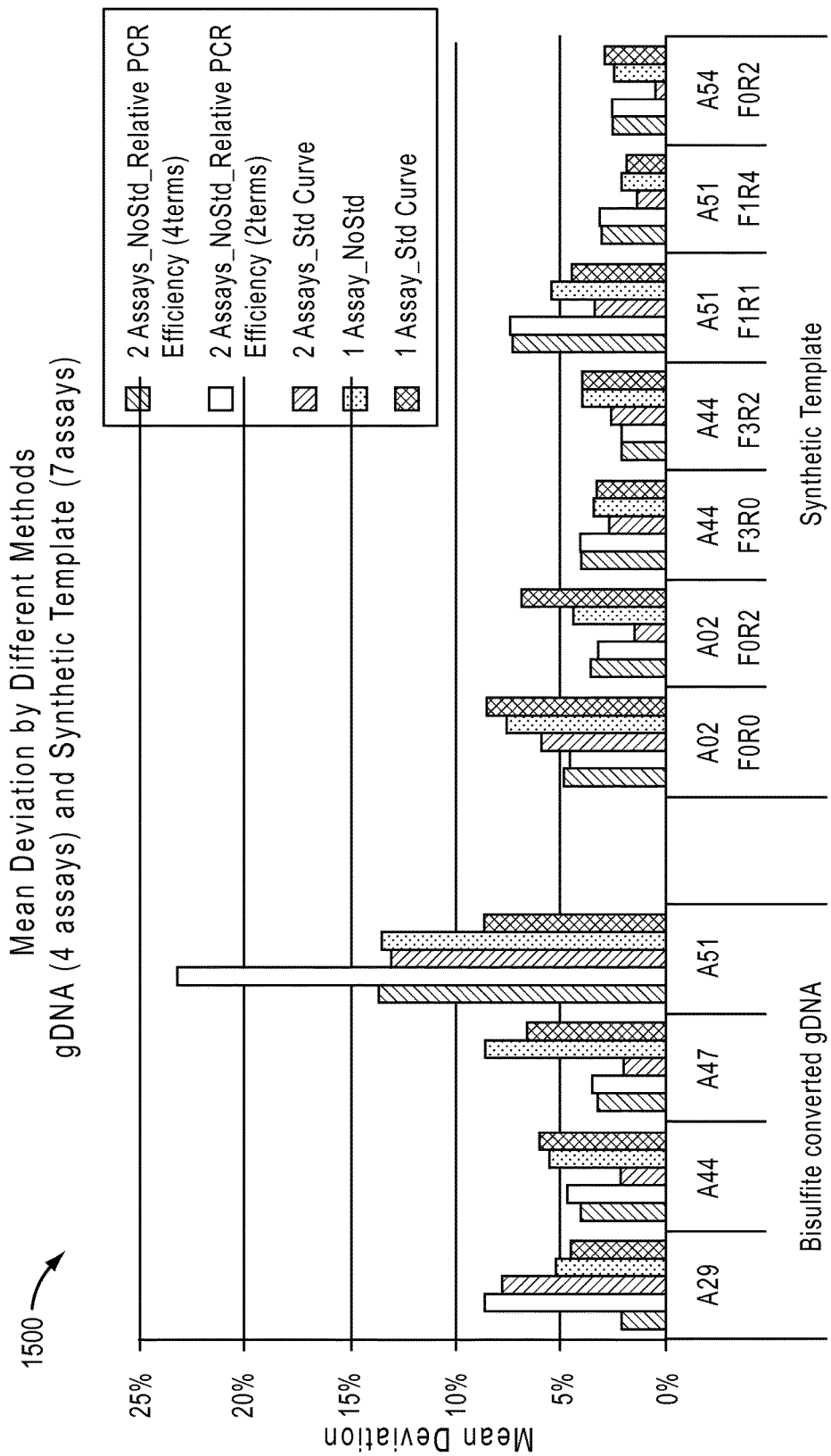
FIG. 15 illustrates mean deviation by different methods with BIS gDNA and synthetic templates according to various embodiments described herein.

FIG. 15 illustrates plot 200 showing the mean deviation by different methods with BIS gDNA and synthetic templates.

CONCLUSION

We have demonstrated here a simple, cost effective and accurate method for methylation level measurement, according to various embodiments. SYBR® Select Master Mix performs well with bisulfite converted gDNA and assays with a wide range of GC content. Consistent and robust amplification with high specificity and excellent discrimination makes it a reliable cost effective option for methylation studies. We have also described a simple quantitative method for accurate measurement of methylation level, with mean bias ≈4%. Without the need of creating standard curves, the workflow and plate design is simplified. Using the Single-Assay method, only two reference runs are needed for the determination of PCR efficiency of Assay1 (or 100% MeC), offering maximum flexibility and simplicity. With the 2-Assay method, the accuracy is higher making it preferable for applications where the relative abundance of two sequences is to be determined.

Figure 18:
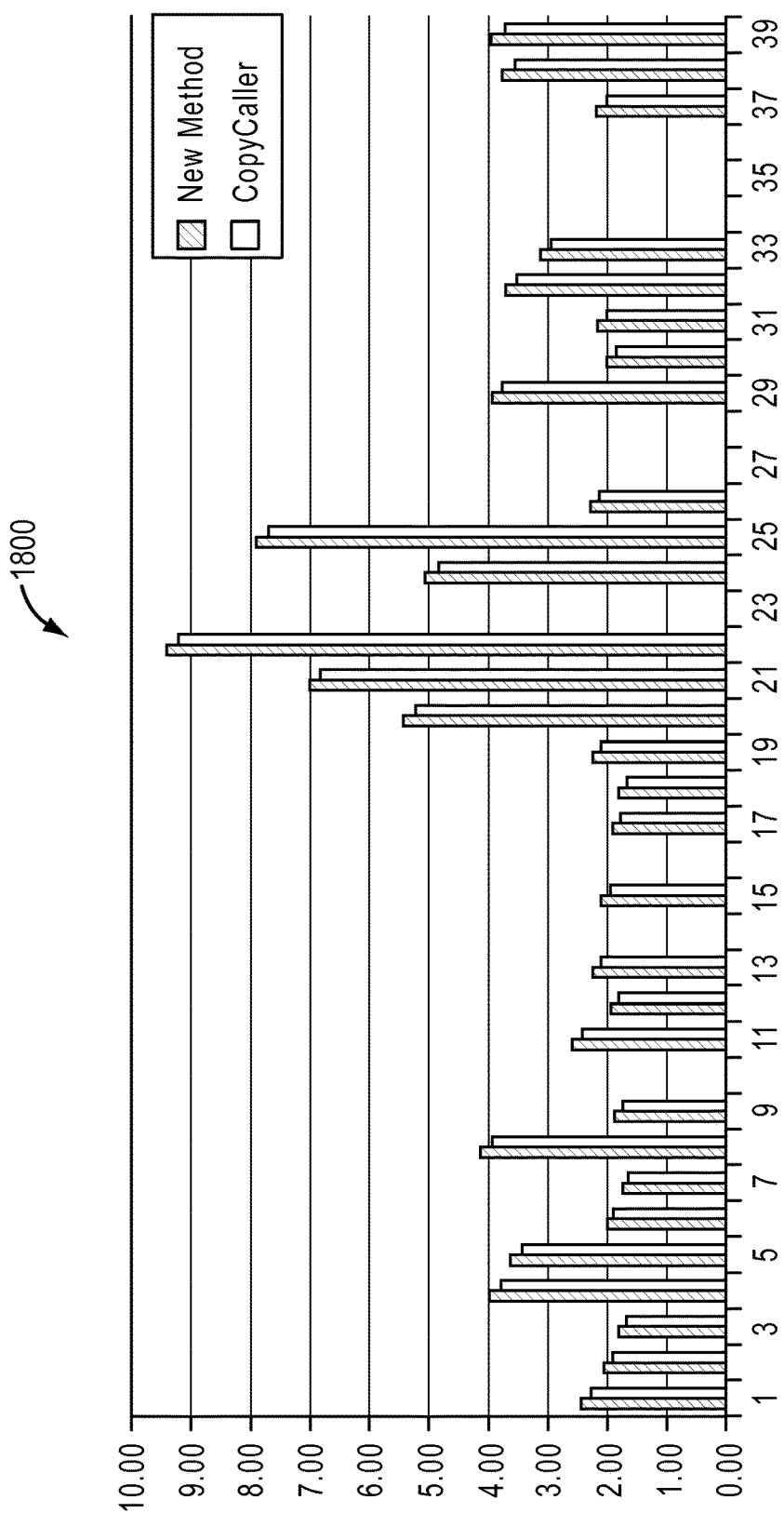
FIG. 18 illustrates a chart of copy number determination using a traditional method vs. the quantitation method according to various embodiments described herein.

According to the present teachings, the quantitation method produces similar results than the quantitation methods currently used. For example, FIG. 18 illustrates a chart of copy number determination using a traditional method vs. the quantitation method according to various embodiments described herein.

Although various embodiments have been described with respect to certain exemplary embodiments, examples, and applications, it will be apparent to those skilled in the art that various modifications and changes may be made without departing from the present teachings.

The invention claimed is:

1. A method for quantitation of biological material in a biological sample, the method comprising:
   receiving amplification data from amplification of a first reference sample (S1) and a second reference sample (S2);
   receiving amplification data from amplification of a biological sample;
   determining a specific PCR efficiency ($\varepsilon$) from the received amplification data from amplification of the first and second reference sample;
   determining a relative PCR efficiency for the for the second reference sample with equation:

$$\varepsilon_{S2A2} = \varepsilon_{S1A1}^{\frac{CT_{100\%S1A1}}{CT_{100\%S2A2}}};$$

and
   determining a quantity of biological material in the biological sample using the relative PCR efficiency and the amplification data received from amplification of the biological sample.

2. The method of claim 1, wherein the amplification of the first and second reference sample is performed with a single primer assay.

3. The method of claim 1, wherein the quantity of biological material relates to a methylation level of the biological sample.

4. The method of claim 3, wherein the methylation level of the biological sample is determined by the following equation:

$$x\% \approx \varepsilon_{S1A1}^{(CT_{R1}-CT_1)} \times 100\%.$$

5. The method of claim 1, wherein the quantity of biological material relates to determining a genotyping result.

6. The method of claim 1, wherein the quantity of biological material relates to determining a copy number variation result.

7. The method of claim 1, further comprising:
   receiving amplification data from amplification of a third reference sample; and
   determining the efficiency from amplification of the first, second, and third reference sample.

8. The method of claim 7, wherein the amplification of the first, second, and third reference sample is performed with a dual primer assay.

9. A non-transitory computer-readable storage medium encoded with processor-executable instructions for quantitation of biological material in a biological sample, the instructions comprising instructions for:
   receiving amplification data from amplification of a first reference sample (S1) and a second reference sample (S2);
   receiving amplification data from amplification of a biological sample;
   determining a specific PCR efficiency ($\varepsilon$) from the received amplification data from amplification of the first reference sample;
   determining a relative PCR efficiency for the second reference sample with equation:

$$\varepsilon_{S2A2} = \varepsilon_{S1A1}^{\frac{CT_{100\%S1A1}}{CT_{100\%S2A2}}};$$

and
   determining a quantity of biological material in the biological sample using the relative PCR efficiency and the amplification data received from amplification of the biological sample.

10. The non-transitory computer-readable storage medium of claim 9, wherein the instructions further comprise instructions for receiving amplification data from amplification of the first and second reference sample performed with a single primer assay.

11. The non-transitory computer-readable storage medium of claim 9, wherein the quantity of biological material relates to a methylation level of the biological sample.

12. The non-transitory computer-readable storage medium of claim 11, wherein the methylation level of the biological sample is determined by the following equation:

$$x\% \approx \varepsilon_{S1A1}^{(CT_{R1}-CT_1)} \times 100\%.$$

13. The computer-readable storage medium of claim 9, wherein the quantity of biological material relates to determining a genotyping result.

14. The computer-readable storage medium of claim 9, wherein the quantity of biological material relates to determining a copy number variation result.

15. The non-transitory computer-readable storage medium of claim 9, wherein the instructions further comprise instructions for:
   receiving amplification data from amplification of a third reference sample; and
   determining the efficiency from amplification of the first, second, and third reference sample.

16. The non-transitory computer-readable storage medium of claim 15, wherein the instructions further comprise instructions for receiving amplification data from amplification of the first, second, and third reference sample performed with a dual primer assay.

17. A system for quantitation of biological material in a biological sample, the system comprising:
   a processor; and
   a non-transitory computer readable memory, wherein the medium comprises processor-executable instructions and wherein the instruction are configured to perform a method when executed, the method comprising:
     receiving amplification data from amplification of a first reference sample (S1) and a second reference sample (S2);
     receiving amplification data from amplification of a biological sample;
     determining a specific PCR efficiency ($\varepsilon$) from the received amplification data from amplification of the first and second reference sample;
     determining a relative PCR efficiency for the for the second reference sample with equation:

$$\varepsilon_{S2A2} = \varepsilon_{S1A1}^{\frac{CT_{100\%S1A1}}{CT_{100\%S2A2}}};$$

and
     determining a quantity of biological material in the biological sample using the relative PCR efficiency and the amplification data received from amplification of the biological sample.

18. The system of claim 17, wherein the amplification of the first and second reference sample is performed with a single primer assay.

19. The system of claim 17, wherein the quantity of biological material relates to a methylation level of the biological sample.

20. The system of claim 19, wherein the methylation level of the biological sample is determined by the following equation:

$$x\% \approx \varepsilon_{S1A1}^{(CT_{R1}-CT_1)} \times 100\%.$$

21. The system of claim 17, wherein the quantity of biological material relates to determining a genotyping result.

22. The system of claim 17, wherein the quantity of biological material relates to determining a copy number variation result.

23. The system of claim 17, wherein the instructions further comprise instructions for:
   receiving amplification data from amplification of a third reference sample; and
   determining the efficiency from amplification of the first, second, and third reference sample.

24. The system of claim 23, wherein the amplification of the first, second, and third reference sample is performed with a dual primer assay.

\* \* \* \* \*